United States Patent [19]
Atkinson et al.

[11] Patent Number: 5,863,775
[45] Date of Patent: Jan. 26, 1999

[54] CONTROL OF PARASITES

[75] Inventors: Howard John Atkinson; Vas Michael Koritsas; Donald Lewis Lee, all of Leeds; Andrew Neilson MacGregor, Canterbury; Judith Elizabeth Smith, Leeds, all of Great Britain

[73] Assignee: The University of Leeds, Leeds, England

[21] Appl. No.: 702,682

[22] PCT Filed: Feb. 28, 1995

[86] PCT No.: PCT/GB95/00419

§ 371 Date: Dec. 20, 1996

§ 102(e) Date: Dec. 20, 1996

[87] PCT Pub. No.: WO95/23229

PCT Pub. Date: Aug. 31, 1995

[30] Foreign Application Priority Data

Feb. 28, 1994 [GB] United Kingdom ............... 9403819

[51] Int. Cl.⁶ .................... C12N 15/63; C12P 21/02; A01H 1/06; A61K 38/16
[52] U.S. Cl. ............ 435/172.3; 435/69.1; 435/69.2; 435/410; 435/412; 514/2; 800/205
[58] Field of Search ................... 435/172.3, 69.1, 435/69.2, 410, 412, 420, 424; 800/205; 514/212.21

[56] References Cited

U.S. PATENT DOCUMENTS

| | | | |
|---|---|---|---|
| 5,066,491 | 11/1991 | Stott et al. | 424/85.8 |
| 5,106,618 | 4/1992 | Beck et al. | 424/85.8 |

FOREIGN PATENT DOCUMENTS

| | | |
|---|---|---|
| 0272144 | 6/1988 | European Pat. Off. |
| 0338229 | 10/1989 | European Pat. Off. |
| 0348348 | 12/1989 | European Pat. Off. |
| 0352052 | 1/1990 | European Pat. Off. |
| 0373771 | 6/1990 | European Pat. Off. |
| 0502730 | 9/1992 | European Pat. Off. |
| 0588122 | 3/1994 | European Pat. Off. |
| 0600396 | 6/1994 | European Pat. Off. |
| 4178335 | 6/1992 | Japan. |
| WO86/00077 | 1/1986 | WIPO. |
| WO88/09384 | 12/1988 | WIPO. |
| WO90/02484 | 3/1990 | WIPO. |
| WO92/04460 | 3/1992 | WIPO. |
| WO92/21753 | 12/1992 | WIPO. |
| WO93/10225 | 5/1993 | WIPO. |
| WO94/15578 | 7/1994 | WIPO. |

OTHER PUBLICATIONS

Nussenzweig et al Malaria Vaccins: Multiple Targets Science 265 1381–1383, 1994.

Masoud, Sameer A., "Expression of a Cysteine Proteinase Inhibitor (oryzacystatin–I) in Transgenic Tobacco Plants," Plant Molecular Biology, 21:655–663, 1993.

Palowski, Asacariasis *In: Tropical and Geographical Medicine*, Warren & Mahmoud, eds, 2nd Edn., McGraw–Hill, New York (1990).

McKee, Nitrogen Metabolism in Plants, Clarendon Press, Oxford (1962).

*Primary Examiner*—Nancy Degen
*Attorney, Agent, or Firm*—William A. Barrett; Steven J. Hultquist

[57] ABSTRACT

The invention relates to a method of combating an animal parasite in a host which comprises delivering an anti-parasitic protein to the parasite or to a locus thereof by administering the protein to the host animal as a medicament or as a food. The anti-parasitic protein may be an inhibitor of an enzyme of the parasite, for example an inhibitor of a digestive enzyme such as a cysteine protease inhibitor. The parasite may be a helminth or a protozoan, for example, a nematode. According to one embodiment the anti-parasitic protein is expressed in a transgenic plant which may be a dietary crop for the host animal.

26 Claims, 11 Drawing Sheets

SEQUENCE LISTING ( 1 ) GENERAL INFORMATION:

( i i i ) NUMBER OF SEQUENCES: 4

( 2 ) INFORMATION FOR SEQ ID NO: 1:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OLIGONUCLEOTIDE"

( x i ) SEQUENCE DESCRIPTION: SEQ ID NO: 1:

ACATGTCGAA TTCTTAGGCA TTTGCACTGG C　　　　　　　　　　　　31

( 2 ) INFORMATION FOR SEQ ID NO: 2:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OLIGONUCLEOTIDE"

( x i ) SEQUENCE DESCRIPTION: SEQ ID NO: 2:

GAGGAGCCCG GGTCGAGCGA CGGA　　　　　　　　　　　　　　24

( 2 ) INFORMATION FOR SEQ ID NO: 3:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OLIGONUCLEOTIDE"

( x i ) SEQUENCE DESCRIPTION: SEQ ID NO: 3:

CTCGAACTCT AGAAGAGAAT TGGCCTTGTT GTG　　　　　　　　33

( 2 ) INFORMATION FOR SEQ ID NO: 4:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "OLIGONUCLEOTIDE"

( x i ) SEQUENCE DESCRIPTION: SEQ ID NO: 4:

AATTCTCTTC TAGAGTTC　　　　　　　　　　　　　　　　　　18

CONTROL OF PARASITES

This invention relates to the control of parasites. More particularly the invention relates to the prophylactic and curative control of animal parasites, such as parasitic nematodes, other helminths, protozoa and all parasites possessing proteases.

Parasites are organisms which are physiologically dependent on one or more host(s) in a relationship which is generally obligatory and where the organism lives at the expense of its host(s). If bacteria, viruses, fungi and rickettsias are excluded, parasites which infect animals (including humans) can be divided into three principal groups: protozoa, helminths (both of which are endoparasitic) and arthropods which are both endo and ectoparasitic. Parasites infect all species of domestic and wild animals as well as humans. Humans are host to over one hundred species of parasite.

Protozoa are unicellular, although they may contain more than one nucleus, and are covered in a plasma membrane as found in other cells. There are at least 45,000 species of protozoa although not all of these are parasitic. Parasitic protozoa include Plasmodium (the causative agent of the disease malaria in humans) which is blood and liver dwelling and transmitted by mosquitoes. At least 300 million people suffer from malaria in tropical and sub-tropical regions. Babesia spp are transmitted by ticks and live in the blood of vertebrates; serious disease is caused in domestic animals, particularly ruminants. Theileria spp. are found in the lymphoid tissue and blood of ruminants and cause diseases including East Coast Fever in cattle. Trypanosoma spp, which cause sleeping sickness in humans and domestic animals, particularly in Africa, mostly live in the blood and tissue fluids of the host and are transmitted by the bite of the tsetse flies. One exception is *T. cruzi* which causes Chagas disease in South and Central America where it infects up to 20 million people. This is transmitted by triatomid bugs. *Leishmania tropica* and *L. major*, spread by sandflies, cause a disfiguring disease, cutaneous leishmaniasis, in humans, while *L. donavani* causes kala azar which may be both disfiguring and life threatening.

It is thought that 100 million people suffer acute or chronic effects of amoebic dysentry and the disease may be responsible for the death of up to 100,000 people per year; amoebic dysentry is due to *Entaamoeba histolytica* an intestinal protozoan parasite. The species is cosmopolitan but in many parts of the tropics and subtropics the prevalence is more than 50% and dysentry is common.

Coccidia cause coccidiosis, a common and serious disease of domestic animals; *Eimeria tenella* which is found in the intestinal cecae of chickens is the best known example, but there are thought to be several important species of coccidia and they occur in other fowl as well as ruminants. Crowded conditions found in batteries can lead to massive infection, which may be severe or fatal. Such is the importance of this group that domestic chickens are maintained on a diet which includes prophylactic drugs (coccidiostats). The US Department of Agriculture estimates that in 1986 $80 million was lost to US farmers in added labour costs and medicated feeds to control coccidiosis. Another coccidian, Toxoplasma, is an intracellular parasite of many tissues particularly in humans and sheep; stillbirths, spontaneous abortions or disability in the new born may result from infection of the foetus. Toxoplasmosis is responsible for one third of all sheep abortions and causes congenital abnormalities in children at the rate of 1 in 2,000 births in the U.K. Toxoplasmosis has been implicated as a cause of death in immunodeficient patients.

*Giardia intestinalis* which lives in the small intestine of humans and *Hexamita meleagridis* in fowl cause highly contagious, diarrhoeal diseases. Infection depends on ingestion of infected water. Giardiasis outbreaks occur frequently in the USA. Trichomonas spp cause a number of disorders of the genito-urinary and digestive system of humans and domestic animals.

Helminth parasites are worms; the group includes the flatworms, such as tapeworms and flukes and the roundworms or nematodes. Again, not all flatworms and nematodes are parasites and of those nematodes which are parasitic, many infect plants and have a major economic effect on many crops. The nematodes vary is size from the microscopic filarial worms to the guinea worms (*Dracunculus medinensis*) which can be up to 80 cm long.

*Ascaris lumbricoides* is estimated to infect one quarter to one third of the human population of the world; it is found predominantly in the tropics and sub-tropics. *Ascaris suum* is a related parasite of pigs and has a wide distribution. These are large worms, 15–50 cm long; as with many parasites their success largely depends on high fecundity and poor levels of sanitation. Eggs are readily dispersed around livestock farms and human communities. They are common in the third world as contaminants of drinking water and fresh produce that has been fertilised with faeces or sewage sludge. Immature Ascaris undergo a migration from the intestine through the liver and lungs before growing to adults in the intestine. There may be pathological consequences of the migratory phase: milk spot causes condemnation of pork livers; juveniles in the lungs may give rise to Loeffler's pneumonia. The most significant pathological consequences are due to the adult nematodes in the intestine. Adult Ascaris consume the contents of the intestine reducing protein, fat and vitamin A uptake and induce an intolerance to milk; in moderate and heavy infections this leads to malnutrition and underdevelopment in children and reduced growth rates in pigs. Other symptoms such as asthma and abdominal pain may arise through allergic responses to Ascaris metabolites. Massive infection can lead to fatal blockage of the intestine and wandering adult worms may block pancreatic or bile ducts. The increase in free range pigs in the United Kingdom in recent years favours a resurgence of Ascariasis in pigs. *Ascaridia galli* is a related species and is a cosmopolitan parasite of chickens. *Toxocara canis* in dogs and *T. cati*, are broadly similar, though their eggs can hatch if ingested by humans and may give rise to visceral larva migrans.

Other nematode parasites of the digestive system include the hookworms such as Ancylostoma and Necator in humans and Bunostomum in ruminants. They attach to the mucosal wall of the intestine and feed on blood and tissue fluids. Infection is through penetration of the skin by juveniles. Trichuris spp. are cosmopolitan though most common in the tropics; they disrupt the caecal mucosa; it is estimated that 700 million humans are infected. Strongyloides spp. are found in the intestinal mucosa of humans and domestic animals. *Heterakis gallinarum* is a cosmopolitan parasite of chickens and other fowl; they live in the caecum and feed on its contents.

The Trychostrongyle nematodes are economically very important parasites of the digestive tract of domestic animals, particularly sheep and cattle: *Haemonchus contortus*, a blood feeder found in the abomasum, causes an acute anaemia in sheep and cattle; Ostertagia spp., which are similarly located, costs the US cattle industry $600 million each year. The principal effects of the latter are due to the migration of juveniles within the gastric glands, resulting in incomplete digestion, fat depletion and malnutrition. Trychostrongylus spp. parasitize the small intestine of many animals including humans causing damage to the mucosa due to burrowing juveniles and feeding adults.

Filarial nematodes are blood or tissue-dwelling. The group includes Onchocerca spp. the causative agent of river blindness, which is particularly-prevalent in West Africa, and related diseases in domestic animals. *Wuchereria bancrofti* and Brugia spp. cause filariasis in humans across a broad equatorial belt; elephantiasis is one form of the disease. Trichinella spp. are also tissue dwelling, being found in muscle, particularly of pigs; human infection may occur through eating inadequately cooked pork.

The most important flatworms belong to the genus Schistosoma; this includes species which are parasitic in humans and domestic animals. At least 200 million people suffer from schistosomiasis (Bilharzia) in the tropics and subtropics. Infection occurs through direct penetration of the skin by the water-dwelling infective stage; thereafter the parasites (which achieve 1–3 cm in length) are blood-dwelling either in the veins around the bladder or the intestine, depending on the species involved. Other economically important flatworms include *Fasciola hepatica*, the liver fluke, a cosmopolitan parasite of the bile ducts of sheep and cattle, and *Dicrocoelium dendriticum* which inhabits the bile ducts of cattle, sheep, goats and pigs. The latter is common throughout most of Europe and North America.

Cestodes, or tapeworms, possess no gut and the body wall or tegument is responsible for digestion and absorption of external nutrients. In several cases, such as *Taenia solium* in humans and pigs and *Echinococcus granulosus* in sheep the principal pathology is due to the larvae in the body tissues of the host. Adult tapeworms which induce a significant pathology include *Diphyllobothrium latum* in humans, where pernicious anaemia may result from infection; this is most common in Baltic countries and is due to eating undercooked fish.

At present, control of parasitic diseases depends largely on the use of drugs, the control of intermediate hosts and improvements in living conditions, particularly sanitation. Drug treatment is generally expensive, and may need to be repeated frequently whether the aim is prophylaxis or cure. In the third world there are often logistical problems about availabilty of diagnostic expertise and appropriate medication and with some drugs medical monitoring is necessary.

Details of the life cycle and pathogenicity of parasites are given in standard texts (see, for example, Schmidt, G. M. and Roberts, L. S. (1989) Foundations of Parasitology, Times Mirror/Mosby College Publishing, St Louis, U.S.A.; Urquhart, G. M. et al (1987) Veterinary Parasitology, Longman Scientific and Technical, London, U.K.).

Proteases are normally divided into four main classes of serine, cysteine (thiol), aspartyl (carboxyl) and metalloproteases (Barrett, 1980). Proteases are involved in important physiological processes that range from protein catabolism or post-translational modification as found in lysosomal metabolism (Kirschke, et al 1980), to involvement in extracellular digestion of dietary proteins.

There has been much interest in the characterisation, cloning and description of the functional significance of proteases in a range of parasites including nematodes, other helminths such as *Schistosoma mansoni* (Chavez-Olortegui et al 1992; *Landsperger* et al 1982), and protozoans, including *Entamoeba histolytica* (Luaces & Barrett, 1988), *Plasmodium falciparum* (Rosenthal & Nelson, 1992), Trypanosoma spp (Eakin et al 1992; Mbawa et al 1992) and *Theileria annulata* (Baylis et al 1992).

Parasite proteases have been studied recently for their roles in infection and nutrition and to explore the potential they offer as targets for vaccine development (McKerrow, 1989). For instance, proteases of all four classes have been reported from animal parasitic nematodes (Sakanari, 1990). The infective larvae of *Dirofilaria immitis* show metalloprotease activity in their secretory/excretory products (Richer et al, 1992). *Nippostrongylus brasiliensis* also possesses this class of proteins in both infective and adult stages. Cysteine proteases occur in adults of *N. brasiliensis* (Healer et al 1991) and two proteases of this class have been cloned for *Haemonchus contortus* (Cox et al, 1990, Pratt et al, 1990). Expression of the proteases of *H. contortus* are developmentally regulated and the protein is present at much higher levels in feeding adults than in the non-feeding, infective larvae (Pratt et al, 1990). In addition, the free-living species *Caenorhabditis elegans* has also been studied and shown to possess both aspartic and cysteine protease activity (Sarkis et al, 1988). Generic oligonucleotide probes were designed for conserved regions of proteases and used to PCR-amplify gene fragments from *C. elegans* and certain parasitic protozoa (Sakanari et al, 1989). The approach led to characterisation of a cysteine protease gene from *C. elegans*. In situ hybridisation has established expression of this gene within the intestinal cells of this animal which strongly suggests a role for this enzyme in digestion (Ray & McKerrow, 1992).

Ascaris has been shown to possess cysteine (Maki and Yanagisawa, 1986) proteases as digestive enzymes in contrast to other classes of proteases used by mammals in protein digestion (Barrett, 1980). Ascaris secretes inhibitors of proteases other than cysteine proteases into the intestinal lumen so lessening nutritional competition from its host (Martzen et al, 1990, Bennett et al, 1992).

Animals are unable to synthesise all the amino acids which they require and so proteins are essential to their nutrition. Proteases are used by animals to break down proteins into smaller molecules (peptides) as part of the assimilation of food. In addition, they are of value to many parasites in assisting the invasion of hosts.

The substrate specificity of proteases from different sources vary and do not provide a basis on which to define them. The enzymes act through four distinct catalytic mechanisms and this allows division into four classes of serine, cysteine, aspartic and metalloproteases. Serine proteases are widespread and diverse and cysteine proteases are also widely distributed and occur in bacteria, microorganisms, plants and animals. The metalloproteases are also widely distributed and occur in bacteria, eukaryotic microorganisms, plants and animals. The aspartic class has a more limited distribution and seems restricted to eukaryotes. A wide range of inhibitors are known but of particular interest are various proteins that are not substrates but inhibitors of such enzymes. These protease inhibitors occur widely, for instance there is a protease inhibitor of cysteine proteases (i.e. a cystatin) in chick egg white and several human and rat cystatins. Many protease inhibitors occur in plants and in particular they accumulate in seeds. The currently recognized plant protease inhibitor (PI) families are Bowman-Birk, Kunitz, potato 1, potato 2, cucurbit, the cereal superfamily, Ragi 1–2, maize 22 kDa and the cystatin family. The cystatin family includes oryzacystatin I and II which occur in rice and a cystatin from maize which is termed zeacystatin herein. Oryzacystatin I has been expressed transgenically in tobacco plants (Masoud et al, 1993) abiablishing the ability of cystatins to be expressed as transgenes.

The natural role of PIs in plants include anti-pathogen or anti-herbivore effects. For instance Cowpea trypsin inhibitor (CPTi) is a double headed serine protease inhibitor for which protein and cDNA sequence is known (EP-A-0 272 144; Hilder et al 1989). There are reports that variation in CPTi levels in seeds can be correlated with field resistance to bruchid beetles suggesting that CPTi protects seeds of Cowpea from herbivory by certain insects. A cassette including a CaMV35S promoter and the coding sequence for a mature CPTi inhibitor has been inserted into tobacco using *Agrobacterium tumefaciens*-mediated transformation. There was a correlation between the level of expression of CPTi and both survival of *Heliothis virescens* and the level of damage caused by these insect larvae to the plants (Hilder et al, 1987; EP-A-0 272 144).

Protease inhibitors such as CPTi have been shown to have protective effects against plant parasitic nematodes such as Globodera and Meloidogyne species. Expression of CPTi in plants suppresses the growth rate, fecundity and sex ratio of these crop pests (EP-A-0 502 730).

EP-A-0 348 348 relates to the production of transgenic plants expressing protease inhibitors to render the plant resistent to pests such as insects, mites, fungi and bacteria (although there is no reference to plant nematodes). Examples include transgenic maize, potatoes, tomatoes, orchard grass, cotton and tobacco expressing serine protease inhibitors and the cysteine protease inhibitor chicken egg white cystatin.

WO 92/21753 relates to the use of so-called midgut effective plant cystatins to control insect pests which attack plants. The specification discloses transgenic plants expressing these cystatins and examples are transgenic maize, rice, cotton, alfalfa, dry bean, potato and rape seed which express potato papain inhibitor.

The use of proteases such as papain in the treatment of intestinal helminth infections including Ascaris has been documented (Pawlowski, 1990) and is derived from the traditional use of leaves and latex of the papaya plant as a vermifuge (McKee, 1962). However, this traditional use of proteases as a vermifuge, which was first reported nearly 200 years ago, is not now regarded as an effective treatment and does not suggest the use of proteins with a specific anti-parasite activity in combating animal parasites.

Pharmaceutical uses for cystatins unrelated to the control of pests have been proposed. EP-A-0373 771 relates to the use of cystatins in the treatment of allergic and bone diseases. WO 88/09384 proposes the use of cystatin C as an anti-viral, anti-bacterial and anti-cancer agent and in the treatment of sciatica and brain haemorrhage. WO 94/15578 relates to oral and edible compositions comprising cystatin S, cystatin SA or cystatin SN where the cystatin is said to have an anti-caries effect. JP-040178335 relates to the use of protease inhibitors including cystatins in the treatment of viral diarrhea in children and domestic animals.

There is clearly still a need for better control of animal parasites. It is an object of the present invention to provide an improved prophylactic and curative approach for parasites in humans and livestock and, in particular, a method which is not dependent on periodic dosing as either a prophylactic or curative measure.

It has now surprisingly been found that prophylactic and curative control of animal parasites can be achieved by administration of an anti-parasitic protein, preferably an inhibitor of an enzyme of the parasite, to the potential host, for example as a medicament or as part of the food of the host. As used herein, references to "combating" an animal parasite are intended to include both prophylactic and curative control of the parasite. It should be understood that as used herein the terms "animal", "mammal" and the like are used in their normal biological sense as including man.

According to one aspect, the present invention provides a method for combating an animal parasite in a host animal which comprises delivering an anti-parasitic protein, preferably an inhibitor of an enzyme of the parasite, to the parasite or to a locus thereof by administering the protein to the host animal as a medicament or as a food.

According to one preferred embodiment of the invention, the anti-parasitic protein is administered orally to the host animal either as part of the food of the animal or as a medicament. However, other suitable modes of administration can be used provided that they result in an effective amount of the anti-parasitic protein being delivered to the locus of the parasite. For example oral administration may be appropriate in the case of a parasite which lives in the intestine of the host animal and consumes the host's food such as Ascaris and Ascaridia. Oral administration may also be appropriate in the case of intestinal parasites which feed on blood or tissue fluids of the host, such as Giardia, Haemonchus and hookworm. Parasites in the intestinal tissues, for example Coccidia and Ostertagia may also be susceptible to an anti-parasitic protein administered by the oral route. Non-intestinal parasites, such as blood and tissue dwelling parasites, may also be susceptible to anti-parasitic protein administered orally provided that an effective amount of the protein can be absorbed into the bloodstream. Alternatively, anti-parasitic protein can be incorporated into a medicament for parenteral administration, for example for use as an injection, or for topical administration. Parasites in skin such as Leishmania and Onchocerca may be particularly susceptible to topical administration of the anti-parasitic protein.

The following is a summary of possible modes of administration of the anti-parasitic protein together with examples of target parasites against which particular modes of administration may be effective:

Administration of an anti-parasite protein to the host animal or its locus as a medicament or as a food or incorporated into food i.e. by oral administration Members of the Order Ascaridata including *Ascaris suum, Ascaris lumbricoides, Ascaridia galli,* Anisakis spp, *Parascaris equorum, Toxocara canis, T. cati, T. vitulorum* and *Toxascaris leonina.*

Trichostrongyles including *Nematodirus battus, Nematodirus spathiger, Nematodirus filicollis, Haemonchus contortus, Trichostrongylus colubriformis, T. tenuis, T. capricola, T. falcatus, T. rugatus, T. axei, Ostertagia ostertagi, O. circumcincta, O. trifurcata, Oesophagostomum radiatum* and *Cooperia cuticei.*

Strongyloids including *Strongyloides stercoralis, S. ransomi* and *S. papillosus.*

Hookworms including *Necator americanis, Ancylostoma duodenale, A. ceylanicum, A. braziliense, A. caninum* and Bunostomum spp.

Members of the Order Trichurata including *Trichuris trichuria, T. suis, T. ovis, Capillaria hepatica, C. annulata, C. caudinflata.*

Oxyurids including *Heterakis gallinarum, Oxyuris equi, Enterobius vermicularis* and *E. gregorii.*

Tapeworms including *Taenia solium, T. saginata, Diphyllobothrium latum, Echinococcus granulosus, E. hydatigena, Hymenolepis diminuta* and *H. nana.*

Trematodes including *Fasciola hepatica, F. gigantea, Fasciolopsis buski, Dicrocoelium dendriticum, Chlonorchis sinensis* and *Opisthorchis felineus.*

Coccidia including *Eimeria acervulina, E. necatrix, E. maxima, E. brunetti, E. tenella, E. meleagrimitis, E. danailova, E. anseris, E. alabamensis, E. bovis, E. zuernii, E. ahsata, E. arloingi, E. debliecki, Isospora belli, Toxoplasma gondii, Sarcocystis hirsuta, S. porcifelis, S. cruzi, S. tenella, S. bertrami, S. fayeri, S. meischeriana, S. suihominis, S. hominis, S. gigantea, Besnoita bennetti, B. wallacei, Hammondia heydorni* and *Cryptosporidium* spp.

Intestinal flagellates including *Giardia intestinalis, Hexamita meleagridis, Histomonas meleagridis, Trichomonas gallinarum, Spironucleus meleagridis* and *Dientamoeba fragilis.*

Amoebae including *Entamoeba histolytica, E. hartmanni, E. gingivalis, E. coli, Endolimax nana, Naegleria fowleri* and *Iodamoeba buetschlii.*

Administration of an anti-parasite protein to the host animal or its locus as a medicament by injection into the bloodstream or tissues Members of the family Sarcocystidae including *Toxoplasma gondii, Sarcocystis hirsuta, S. porcifelis, S. cruzi, S. tenella, S. bertrami, S. fayeri, S. meischeriana, S. suihominis, S. hominis, S. gigantea, Besnoita bennetti, B. wallacei* and *Hammondia heydorni.*

Other protozoa including *Trypanosoma brucei, T. brucei brucei, T. brucei gambiense, T. brucei rhodesiense, T. congolense, T. vivax, T. cruzi, T. equiperdum, T. equinum, T. evansi, T. rangeli, T. theileri, Leishmania tropica, L. tropica tropica, L. tropica major, L. aethiopica, L. donavani, L. donavani donavani, L. donavani archibaldi, L. donavani infantum, L. donavani chagasi, L. mexicana, L. mexicana mexicana, L. mexicana amazonensis, L. mexicana pifanoi, L. mexicana aristedesi, L. mexicana garnhami, L. braziliensis, L. braziliensis braziliensis, L. braziliensis guyanensis, L. braziliensis panamensis, L. peruviana, L. enriettii, L. hertigi, L. hertigi hertigi, L. hertigi deanei, L. aethiopica, Trichomonas vaginalis, T. tenax, T. foetus, Pentatrichomonas hominis, Plasmodium vivax, P. falciparum, P. ovale, P. malariae, P. gallinaceum, Babesia bigemina, B. bovis, B. berbera, B. divergens, B. argentina, B. major, B. caballi, B equi, B. ovis, B. motasi, B. traumanni, B. canis, B. gibsoni, B felis, Theileria parva, T. annulata, T. mutans, T. hirei, T. sergenti, T. hirci, T. ovis* and *Haematoxenus veliferous.*

Filarial nematodes including *Wuchereria bancrofti, Brugia malayi, Onchocerca vovulus, O. gutterosa, O. gibsoni, Loa loa, Dipetalonema perstans, D streptocerca, Mansonella ozzardi* and *Dirofilaria imitis.*

Members of the Order Trichurata including *Trichinella spiralis* and *T. psuedospiralis.*

Trematodes including *Schistosoma mansoni, S. haematobium, S. japonicum, S. mekongi, S. matthei, S. intercalatum, S. bovis, Fasciola hepatica, F. gigantea, Fasciolopsis buski, Dicrocoelium dendriticum, Chlonorchis sinensis* and *Opisthorchis felineus.*

Metastrongyles including *Dictyocaulus viviparis, D. filaria, D. arnfieldi* and *Angiostrongylus cantonensis.*

Tapeworms including *Taenia solium, T. saginata, Diphyllobothrium latum, Echinococcus granulosus, E. hydatigena, Hymenolepis diminuta* and *H. nana.*

Members of the Order Ascaridata including *Toxocara canis, T. cati, T. vitulorum* and *Toxascaris leonina.*

Guinea worms including *Dracunculus medinensis.*
Administration of an anti-parasite protein to the host animal or its locus as an ointment or cream for topical application Filarial nematodes including *Onchocerca vovulus, O gutterosa, O. gibsoni, Loa loa, Dipetalonema streptocerca, Mansonella ozzardi.*

Leishmania species including *Leishmania tropica, L. tropica tropica, L. tropica major, L. aethiopica, L. donavani, L donavani donavani, L. donavani archibaldi, L. donavani infantum, L. donavani chagasi, L. mexicana, L. mexicana mexicana, L. mexicana amazonensis, L. mexicana pifanoi, L mexicana aristedesi, L. mexicana garnhami, L. braziliensis, L braziliensis braziliensis, L. braziliensis guyanensis, L braziliensis panamensis, L. peruviana, L. enriettii, L hertigi, L. hertigi hertigi, L. hertigi deanei, L. aethiopica.*

Guinea worms including *Dracunculus medinensis.*

Administration of an anti-parasite protein to the host animal or its locus as a pessary

*Trichomonas vaginalis.*

For example, the anti-parasitic protein may be an inhibitor of a digestive enzyme of the parasite, such as a cysteine protease inhibitor. The animal parasite may be a helminth, for example a nematode, or a protozoan. Preferably the anti-parasitic protein is an inhibitor of a class of protease found in the parasite but not at the locus of the parasite in the host.

As noted above, it has already been proposed that protease inhibitors such as CPTi have protective effects against insects (EP-A-0 272 144, EP-A-0 348 348 and WO 92/21753) and plant parasitic nematodes such as Globodera and Meloidogyne species (EP-A-0 502 730). However, there are such large differences between the physiology, mode of nutrition and environment of both herbivorous insects and plant pathogens, and that of any animal parasites that it could not have been predicted that a protease inhibitor effective against any insect species or plant pathogen would show efficacy against any animal parasite. In addition any protective role of a plant protease inhibitor against either a herbivore or a pathogen can have no such benefit for the plant against animal parasites with which it does not interact. The plant parasitic nematodes used in previous work (EP-A-0 502 730) modify plant cells to form specialised feeding sites and their nutrition is very different from that shown by most animal parasitic nematodes. It was therefore quite unpredictable that a particular protease inhibitor, even one that influences a pathogen or herbivore including plant parasitic nematodes feeding in roots, would also influence animal parasites including nematodes when the plant is ingested by livestock or humans.

As used herein the term "anti-parasitic protein" means a protein which has a specific anti-parasitic action by a mechanism not involving the host immune system. Some activity against the host may not be precluded in some cases but the action against the parasite must be sufficiently specific for the protein to be useful in combating the parasite. Proteins which cause non-specific damage to host and parasite alike are excluded. The anti-parasitic protein used according to the present invention is preferably an inhibitor of a digestive enzyme of the parasite, for example an inhibitor of plant or animal origin. The protease inhibitor may be a cysteine protease inhibitor, such as a cysteine protease inhibitor from maize. Other suitable plant cysteine protease inhibitors include those from rice, papaya, potato, Wisteria, soybean, pineapple, broom or other legumes or other plant species. Alternatively, the protease inhibitor is or has significant structural and functional similarity to a cysteine protease inhibitor from animal or other sources such as chicken egg white cystatin, human cystatin A, human cystatin B, human cystatin C, human cystatin S, rat cystatin $\alpha$, rat cystatin $\beta$, kininogen, L-kininogen and H-kininogen.

Protease inhibitors such as the cystatins from maize and rice occur in seeds of these plants and not in the roots of these plants where nematodes such as Meloidogyne occur. Therefore it is surprising that these stored seed proteins are effective against animal parasites even after their oral uptake by the host. The protease inhibitor must survive passage to the locus of the parasite and be taken up in levels that show an effect against the parasites. This is very different from demonstrating an effect against a plant parasitic nematode for a protease inhibitor expressed by its host i.e. a plant.

As already indicated, the protease inhibitor is preferably effective against a class of proteases found in the parasite but not at the locus of the parasite in the host, for example an inhibitor of a class of proteases found in intestinal nematodes but not in the vertebrate intestine. The cystatins fall within this class but whilst there are no proteases in the mammalian intestine likely to be inhibited by cystatins, there are cysteine proteases elsewhere in the mammalian body so that care will be needed that intravenous administration of cystatins does not produce an unacceptable toxicological hazard. Administration of other classes of protease inhibitors may be less hazardous and thus more appropriate for tissue dwelling parasites.

The anti-parasitic protein used according to the present invention may also be an antibody acting on the parasite without involvement of the host immune system either in the production of the antibody or its action against the parasite. For example, the antibody could bind to and thereby block the active site of an enzyme of the parasite. The enzyme can be a digestive enzyme (protease) of the parasite, in which case the antibody can also be regarded as a protease inhibitor, or can be an enzyme with another function vital to the parasite. Such antibodies will generally be monoclonal antibodies and can be produced by conventional hybridoma technology and can be modified in various ways as desired, for example by removal of a region of the antibody such as the Fc region. The anti-parasitic protein may also be an antibody specific for an antigen expressed by the parasite and which has been modified to conjugate an antibody protein specific for a parasite with a toxin for the parasite. Suitable monoclonal antibodies, optionally conjugated with a toxin, can be produced by conventional methods of recombinant DNA technology.

Recent work has established the potential of plant biotechnology for medical applications in that antibodies have been expressed in plants (Hiatt et al 1989, During et al 1990) and use of these antibodies for passive immunisation has been suggested (Haitt & Ma, 1992). The Hepatitis B. surface antigen (Mason et al 1992), the non-toxic β-chain of cholera toxin and antigens from *Streptococcus mutans* and *Escherichia coli* have been expressed in plants as a future basis for administering oral vaccines (reported by Moffat, 1993). This approach is very distinct from the present invention which does not envisage use of proteins that act via the immune system by initiating an immune response as immunogens do within a vaccine. Oral vaccines act in this way after ingestion of the antigen. The anti-parasitic proteins according to the present invention may be antibodies produced by the mammalian immune system or by use of hybridoma technology which may optionally be modified, and which may subsequently be engineered into plants, and which act directly on the parasite without involvement of the host immune system. Such antibodies are less likely to suffer from the problems of degradation in the gut which arise in the development of an oral vaccine or an antibody for the induction of passive immunity. In addition protease inhibitors are also able to withstand passage through the mammalian or avian gut system without loss of activity.

According to one embodiment of the invention, the anti-parasitic protein is expressed by a transgenic plant. The means by which transgenic plants expressing heterologous proteins throughout the plant or at various locations or at various stages of their life-cycle are known. In addition, transgenic plants have already been produced expressing protease inhibitors as a means of protecting the plant against plant parasites (see EP-A-0 272 144, EP-A-0 348 348, WO 92/21753 and Masoud et al, 1993). The same methods can be used to produce transgenic plants expressing anti-parasitic proteins, for example cysteine protease inhibitors of plant or animal origin.

Without wishing to be bound by specific methodology, an example of the steps required to produce a transgenic plant expressing an anti-parasitic protein is as follows:

isolation of MRNA from a suitable source and preparation of CDNA encoding the anti-parasitic protein using standard techniques of cDNA cloning;

transfer of the CDNA encoding the anti-parasitic protein into an expression cassette including a promoter and other regulatory elements suitable for use in the intended host plant;

transfer of the expression cassette into a transgenesis vehicle suitable for infection of the intended host plant, e.g. *Agrobacterium tumefaciens*;

Infection of the intended host plant with the transgenesis vehicle.

Many alternatives exist for the steps referred to above and in some cases some of the steps may already have been carried out, for example, cDNA encoding the anti-parasitic protein may already exist. For example, protease inhibitors can be expressed constitutively using a promoter such as CaMV35S but in addition some of the more efficacious inhibitors as described herein can be produced in a manner which enhances efficacy by confining expression to part only of the transgenic plant. For example in the case of a protease inhibitor produced naturally only in the seeds of the plant in which it occurs, the promoters naturally occurring in the gene encoding the protease inhibitor can be used to control expression to just seeds of the transgenic plant.

Suitable plants which can be transformed with DNA encoding the anti-parasitic protein include dietary crops for the intended host of the animal parasite, such as fruit crops, vegetables and tubers, oil crops, sugar crops, forage legumes. Fiber plants and woods and drug crops can also be used.

Suitable plants which can be transformed with DNA encoding anti-parasitic protein, classified according to the use of the plants, are set out in the following Table A.

TABLE A

Plant Classification According to Use

CEREALS

Monocot

| | |
|---|---|
| *Avena nuda* (chinensis) | Chinese naked oat |
| *A. sativa* | Common oats |
| *Aleusine coracan* | African millet |
| *Eragrostis tef* | Tef grass |
| *Hordeum distichum* | Two-row barley |
| *H. vulgare* | Barley |
| *Oryza sativa* | Rice |
| *Panicum italicium* | Italian millet |
| *P. miliaceum* | Broomcorn millet |
| *pennisetum glaucum* | Spiked millet |
| *P. spicatum* (americanum) | Pearl millet |
| *Secale cereale* | Rye |
| *Sorghum vulgare* | Grain sorghums |

TABLE A-continued

Plant Classification According to Use

| | |
|---|---|
| *Triticala hexaploide* | Triticale |
| *Triticum aestivum* | Common wheat |
| *T. dicoccum* | Emmer |
| *T. durum* | Abyssinian hard wheat |
| *T. monococcum* | Einkorn wheat |
| *Zea mays* | Starch, sweet corn |
| Dicot | |
| *Amaranthus paniculatus* | Grain amaranth |
| *Fagopyrum esculentum* | Buckwheat |
| *F. tataricum* | Rye buckwheat |
| LEGUMES | |
| Dicot | |
| *Arachis hypogea* | Peanut, groundnut |
| *Cajanus indicus* | Pigeon pea |
| *Cicer arietinum* | Chickpea |
| *Dolichos lablab* | Hyacinth bean |
| *Glycine gracilas* | Manchurian soya |
| *G. max* | Soybean |
| *G. ussuriensis* | Wild soya |
| *Lathyrus sativus* | Grass pea |
| *Lens culinaris* | Lentil |
| *Mucuna pruriens* | Cowitch, Florida velvet bean |
| *Phaseolus acutifolius* | Tepary bean |
| *P. aureus* | Mung, green gram |
| *P. lunatus* | Lima bean, Sieva |
| *P. coccineus* (multiflorus) | Scarlet runner bean |
| *P. mungo* | Mung bean, black gram |
| *P. vulgaris* | French, common, kidney or dwarf bean |
| *Pisum sativum* | Pea |
| *Vicia faba* | Broad bean, horse bean, field bean |
| *Vigna angularis* | Adzuki bean |
| *V. radiata* | Mung bean |
| *V. sesquipedalis* | Asparagus bean, yard-long bean |
| *V. sinensis* | Cowpea |
| FRUIT CROPS | |
| Dicots | |
| *Amygdalus communis* | Almond |
| *Ananas comosus* | Pineapple |
| *Artocarpus communis* | Breadfruit |
| *Carica papaya* | Papaya |
| *Citrullus vulgaris* | Watermelon |
| *Citrus grandis* | Pummelo |
| *C. medica* | Lemon, citron |
| *C. nobilis* | Tangerine |
| *C. reticulata* | Mandarin |
| *C. sinensis* | Orange |
| *Cydonia oblonga* | Quince |
| *Diospyros kaki* | Japanese persimmon |
| *Ficus carica* | Fig |
| *Fragaria chiloensis* | Wild strawberry |
| *F. virginiana* | Strawberry |
| *Litchi chinensis* | Lychee |
| *Malus asiatica* | Chinese apple |
| *M. pumila* | Apple |
| *Mangifera indica* | Mango |
| *Morus rubra* | Red mulberry |
| *Musa cavendishii* | Banana |
| *M. paradisiaca* | Banana |
| *Passiflora edulis* | Passion fruit, purple granadilla |
| *Persea americana* | Avocado pear |
| *P. ligularis* | Passion flower |
| *Phoenix dactylifera* | Date palm |
| *Prunus armeniaca* | Apricot |
| *P. avium* | Sweet cherry, mazzard |
| *P. cerasifera* (divaricata) | Cherry plum |
| *P. cerasus* | Cherry |
| *P. domestica* | European plum or prune |
| *P. maheleb* | Maheleb cherry |
| *P. persica* | Peach and nectarine |
| *P. pseudocerasus* | Cherry |
| *P. salicinia* | Japanese peach |
| *P. serotina* | Wild black cherry |
| *Psidium guajava* | Guava |
| *Punica granatum* | Pomegranate |
| *Pyrus communis* | Pear |
| *P. ussuriensis* | Chinese pear |
| *Ribes grossularia* | Gooseberry |
| *R. nigrum* | Blackcurrant |
| *R. rubrum* | Red currant, white currant |
| *Rubus idaeus* | European raspberry |
| *R. strigosus* | American raspberry |
| *Tamarindus indica* | Tamarind |
| *Vaccinium angustifolium* | Sugarberry |
| *V. ashei* | Rabbiteye blueberry |
| *V. corymbosum* | Highbush blueberry |
| *V. myrtillus* | Canada blueberry |
| *V. oxycoccos* | Cranberry |
| *Viburnum trilobum* | American cranberry |
| *Vitis labrusca* | Fox grape |
| *V. vinifera* | Grape |
| VEGETABLES AND TUBERS | |
| Monocot | |
| *Allium ascalonicum* | Shallot, green onion |
| *A. cepa* | Onion |
| *A. chinense* | Onion |
| *A. fistulosum* | Welsh onion |
| *A. porrum* | Leek |
| *A. sativum* | Garlic |
| *A. schoenoprasum* | Chives |
| *Asparagus officinalis* | Asparagus (var. attilis) |
| *Zea mays* | Sweet corn |
| Dicot | |
| *Amoracia lapathifolia* | Horseradish |
| *Apium graveolens* | Celery |
| *Arabidopsis thaliana* | Common wall cress, thale cress |
| *Beta vulgaris* | Sugar, mangold or garden beet |
| *Brassica alboglabra* | Chinese kale |
| *B. campestris* | Turnip rape |
| *B. carinata* | Abyssinian mustard |
| *B. cernua* | Karashina |
| *B. chinensis* | Chinese mustard or pak-choi |
| *B. hirta* | White mustard |
| *B. juncea* | Brown mustard, pai |
| *B. kaber* | Charlock |
| *B. napobrassica* (rutabaga) | Swede |
| *B. napus* | Rape, oilseed rape, kale |
| *B. nigra* | Black mustard |
| *B. oleracea* | Cole, kale, collards brussel sprouts, cauliflower, cabbage, kohlrabi, broccoli |
| *B. pekinensis* | Chinese cabbage or celery cabbage |
| *B. rapa* | Turnip |
| *Cajanus cajan* (indicus) | Pigeon pea |
| *Canavalia ensiformis* | Jack bean |
| *Canna edulis* | Edible canna |
| *Capiscum annuum* | Common cultivated pepper |
| *C. chinense* | Pepper |
| *C. frutescens* | Cayenne pepper |
| *C. pendulum* | Pepper |
| *C. pubescens* | Pepper |
| *Cichorium endivia* | Endive |
| *C. intybus* | Chicory |
| *Colocasia antiquorum* | Taro |
| *Crambe maritima* | Sea kale |
| *Cucumis melo* | Melon, cantaloupe |

TABLE A-continued

Plant Classification According to Use

| | |
|---|---|
| *C. sativus* | Cucumber |
| *Cucurbita ficifolia* | Malabar gourd |
| *C. foetidissima* | Calabazilla, buffalo gourd |
| *C. maxima* | Pumpkin |
| *C. moschata* | Winter pumpkin |
| *C. pepo* | Summer squash, vegetable marrow |
| *Cynara scolymus* | Globe artichoke |
| *Daucus carota* | Carrot |
| *Dioscorea slata* | Yam |
| *D. batatas* | Chinese yam |
| *D. cayennensis* | Attoto yam |
| *Eruca sativa* | Rocker salad, rocket or roquette |
| *Ipomea batatas* | Sweet potato |
| *Lactuca sativa* | Lettuce |
| *Lepidium sativum* | Garden cress |
| *Lycopersicon cerasiforme* | Cherry tomato |
| *L. esculentum* | Tomato |
| *Mahihot utilissima* | Manioc, cassava |
| *Nasturtium officinale* | Water cress |
| *Pastinaca sativa* | Parsnip |
| *Petroselinum crispum (sativum)* | Parsley |
| *Physalis peruviana* | Ground cherry |
| *Pisum sativum* | Pea |
| *Raphanus sativus* | Radish |
| *Rheum officinale* | Rhubarb |
| *R. rhaponticum* | English rhubarb |
| *Scorzonera hispanica* | Black salsify |
| *Sechium edule* | Chayote |
| *Solanum andigenum* | Andean potato |
| *S. melongena* | Egg plant |
| *S. muricatum* | Pepino |
| *S. phureja* | Potato |
| *S. tuberosum* | Common potato |
| *Spinacia oleracea* | Spinach |
| NUTS | |
| Dicot | |
| *Anacardium occidentale* | Cashew |
| *Arachis hypogea* | Peanut |
| *Carya illinoinensis* | Pecan |
| *C. ovata* | Shagbark hickory |
| *Castanea sativa* | Chestnut |
| *Cocos nucifera* | Coconut palm |
| *Corylus americana* | American hazel, filbert |
| *C. avellana* | European hazel, cobnut |
| *Juglans nigra* | Black walnut |
| *J. regia* | English walnut |
| *J. sinensis* | Walnut |
| *Litchi chinensis* | Lychee |
| *Macadamia integrifolia* | Queensland nut |
| *Pistacia vera* | Pistachio nut |
| *Prunus amygdalus* | Almond |
| OIL CROPS (COOKING OR VEGETABLE OILS) | |
| Monocot | |
| *Zea mays* | Corn |
| Dicot | |
| *Aleurites cordata* | Tung, China wood oil |
| *A. moluccana (triloba)* | Candlenut |
| *Arachis hypogea* | Ground nut, peanut |
| *Brassica campestris* | Rapeseed oil, canola oil |
| *B. napus* | Rapeseed oil, canola oil |
| *Cannabis sativa* | Hempseed oil |
| *Carthamus tinctorius* | Safflower oil, false saffron |
| *Cocos nucifera* | Coconut palm |
| *Elaeis guineensis* | Oil palm |
| *Glycine gracilis* | Manch, soya |
| *G. max* | Soybean |
| *G. ussuriensis* | Wild soya |
| *Gossypium hirsutum* | Cottonseed oil |
| *Helianthus annus* | Sunflower |
| *Linum usitatissimum* | Flax |
| *Olea europaea* | Olive |
| *Papaver somniferum* | Poppy seed |
| *Ricinus communis* | Castor bean |
| *Sesamum indicum* | Sesame |
| SUGAR CROPS | |
| Monocot | |
| *Saccharum officinarum* (officinarum x spontaneum) | Sugarcane |
| *S. robustum* | Sugarcane |
| *S. sinense* | Sugarcane |
| *S. spontaneum* | Kans grass |
| *Sorghum dochna* | Sorgo syrup, sugar sorghum |
| Dicot | |
| *Acer saccharum* | Sugar maple |
| *Beta vulgaris* | Sugar or mangold beet |
| FORAGE AND TURF GRASSES | |
| Monocot | |
| *Agropyron cristatum* | Crested wheatgrass |
| *A. desertorum* | Crested wheatgrass |
| *A. elongatum* | Tall wheatgrass |
| *A. intermedium* | Intermediate wheatgrass |
| *A. smithii* | Western wheatgrass |
| *A. spicatum* | Blue bunch wheatgrass |
| *A. trachycaulum* | Slender wheatgrass |
| *A. trichophorum* | Pubescent wheatgrass |
| *Alopecurus pratensis* | Meadow foxtail |
| *Andropogon gerardi* | Big bluestem |
| *Arrhenatherum elatius* | Tall oat grass |
| *Bothriochloa barbinodis* | Cane bluestem |
| *B. ischaemum* | King ranch bluestem |
| *B. saccharoides* | Silver bluestem |
| *Bouteloua curipendula* | Side oats grama |
| *B. eriopoda* | Black grama |
| *B. gracilis* | Blue grama |
| *Bromus erectus* | Upright brome |
| *B. inermis* | Smooth brome |
| *B. riparius* | Meadow brome |
| *B. unioloides* | |
| *Cenchrus ciliaris* | Buffel grass |
| *Chloris gayana* | Rhodes grass |
| *Cymbopogon nardus* | Citronella grass |
| *Cynodon dactylon* | Bermuda grass |
| *Dactylis glomerata* | Cocksfoot, orchard grass |
| *Dichanthium annulatum* | Kleberg bluestem |
| *D. aristatum* | Angleton bluestem |
| *D. fecundum* | |
| *D. sericeum* | Silky bluestem |
| *Digitaria decumbens* | Pangola grass |
| *D. smutsii* | |
| *Elymus angustus* | Altai wild rye |
| *E. junceus* | Russian wild rye |
| *Eragrostis curvula* | Weeping love grass |
| *Festuca arundinacea (elation)* | Tall fescue |
| *F. ovina* | Sheeps fescue |
| *F. pratensis* | Meadow fescue |
| *F. rubra* | Red fescue |
| *Lolium multiflorum (italicum)* | Italian ryegrass |
| *L. perenne* | Perennial ryegrass |
| *L. rigidum* | |
| *Panicum maximum* | Guinea grass |
| *P. americanum* | |
| *P. purpurascens* | Para grass |
| *P. virgatum* | Switchgrass |
| *Paspalum dilatatum* | Dallis grass, large water grass |
| *P. notatum* | Bahia grass |
| *Pennisetum clandestinum* | Kikuyu grass |

TABLE A-continued

Plant Classification According to Use

| | |
|---|---|
| P. purpureum | Dry napier grass |
| Phalaris arundinacea | Reed canary grass |
| Phleum bertolinii | Timothy |
| P. pratense | Timothy |
| Poa fendleriana | Mutton grass |
| P. nemoralis | Wood meadow grass |
| P. pratensis | Kentucky bluegrass, smooth stalked meadow grass |
| P. trivialis | Rough stalked meadow grass |
| Setaria sphacelata | Rhodesian timothy |
| S. anceps | |
| Sorghastrum nutans | Indian grass |
| Sorghum halepense | Johnson grass |
| S. sudanense | Sudan grass |
| S. vulgare | Great millet |
| FORAGE LEGUMES | |
| Dicot | |
| Coronilla varia | Crown vetch |
| Crotalaria juncea | Sunn hemp |
| Desmodium intortum | |
| D. heterophyllum | |
| D. sandwicense | |
| D. uncinatum | |
| Digitaria decumbens | |
| Glycine wightii | |
| Lespedeza stipulacea | Korean lespedeza |
| L. striata | Common lespedeza |
| L. sericea | |
| Lotononis bainesii | |
| Lotus corniculatus | Birdsfoot trefoil |
| L. major | |
| L. uliginosus | |
| Lupinus albus | Wolf bean, white lupin |
| L. angustifolius | Blue lupin |
| L. luteus | European yellow lupin |
| L. mutabilis | South American lupin |
| Macroptiliom atropurpureum | |
| Medicago arabica | Spotted burr-clover |
| M. arborea | Tree alfalfa |
| M. falcata | Yellow lucerne |
| M. hispida | Carlifornia burr-clover |
| M. littoralis | |
| M. polymorpha | |
| M. sativa | Alfalfa |
| M. tribuloides | Barrel medic |
| M. trunculata | |
| Melilotus albus | White sweet clover |
| M. officinalis | Yellow sweet clover |
| Onobrychis viciifolia | Sainfoin |
| Ornithopus sativus | Serradella |
| Pueraria thunbergiana | Kudza vine |
| Stylosanthes guyanensis | |
| S. lamata | |
| S. lumitis | |
| Trifolium alexandrinum | Egyptian clover |
| T. augustifolium | Fineleaf clover |
| T. diffusum | Rose clover |
| T. fragiferum | |
| T. hybridum | Alsike clover |
| T. incarnatum | Cromson clover |
| T. ingrescens | Ball clover |
| T. pratense | Red clover |
| T. repens | White clover |
| T. resupinatum | Persian clover |
| T. subterraneum | Subterranean clover |
| Trigonnela foenum-graecum | Fenugreek |
| Vicia sativa | Common vetch |
| V. villosa | Hairy vetch |
| V. atropurpurea | Purple vetch |
| V. angustifolia | Narrowleaf vetch |
| V. dasycarpa | Wooly pod vetch |
| V. ervilia | Monantha (bitter) vetch |
| V. pannonica | Hungarian vetch |
| V. calcarata | Bard vetch |
| FIBER PLANTS AND WOODS | |
| Monocot | |
| Bambusa vulgaris | Bamboo |
| Dicot | |
| Agave sisalena | Sisal hemp |
| Boehmeria nivea | Rhea fibre, ramie |
| Cannabis indica | Hemp |
| C. sativa | Hemp |
| Ceiba pentandra | Silk cotton tree, kapok |
| Corchorus mucronata (striata) | Hemp |
| Gossypium arboreum | Tree cotton |
| G. barbadense | Egyptian cotton |
| G herbaceum | Cotton |
| G. hirsutum | Upland cotton |
| G. manking | Oriental cotton |
| Linum angustifolium | Wild flax |
| L. usitatissimum | Flax |
| Musa textiles | Manila hemp, abaca |
| DRUG CROPS | |
| Dicot | |
| Angelica archangelica | Angelica |
| Chrysanthemum cinerariifolium | Palm pyrethrum |
| Camellia sinensis | Chinese tea |
| C. coccineum | Pyrethrum |
| Coffea arabica | Coffee |
| C. canephora | Quillow coffee |
| Cola acuminata | Kola nut |
| Nicotiana rustica | Tobacco |
| N. tabacum | Tobacco |
| Papaver dubium | Poppy |
| P. somniferum | Opium poppy |
| Theobroma cacao | Cocoa |
| SPICES AND FLAVOURINGS | |
| Monocot | |
| Vanilla fragrans | Vanilla |
| Dicot | |
| Artemisa dracunculus | Tarragon |
| Cinnamomum zeylanicum | Cinnamon |
| Hibiscus esculentus | Okra |
| Salvia officinalis | Sage |
| Thymus vulgaris | Thyme |
| Pimpinella anisum | Anise |
| Metha arvensis | Menthol |
| M. piperita | Peppermint |
| M. viridis | Spearmint |
| Coriandrum sativum | Coriander |

Most of the crops mentioned in the above table can be used as human foods except for the forage and wood crops.

Depending on the nature of the plant, the transgenic plant can be administered directly to the intended host of the animal parasite as food or can be processed to yield a medicament. Where the transgenic plant is administered as a food, the plant will generally already be used as a food or a source of food for the animal in question and the plant can be eaten directly by the animal or processed in the usual way for that plant. In the case of a transgenic plant intended to yield a medicament, the plant can be processed in an appropriate manner, for example, to concentrate or extract the anti-parasitic protein, which may then be formulated into a composition, optionally with appropriate excipients.

The following Table B sets out examples of food crops of domestic animals and crops for which animal feed is derived, classified by the type of animal.

TABLE B

Examples of Food Crops of Domestic Animals and Crops from which Animal Feed is Derived Poultry
  alfalfa, artichokes, barley, beans, broomcorn, buckwheat, cabbage, carrots, cassava, clover, coconut, cotton seed, cowpea, field bean, flax seed, hemp seed, kale, lentils, lettuce, linseed, lucerne, lupin, maize, mangold, millet, oat, parsnip, pea, peanut, potato, rape, rice, rutabagas, rye, sorghum, soy bean, sugar beet, sugar cane, sunflower, swede, turnip, velvet bean, wheat.

Pig
  alfalfa, barley, brussel sprout, buckwheat, cabbage, carrots, cassava, castor bean, coconut, cottonseed, field bean, kale, kapok, kohlrabi, lentil, lucerne, lupins, maize, mangold, mung bean, mustard, oat, palm kernel, parsnip, peanut, peas, potato, pumpkin, rapeseed, rice, rye, safflower, salseed, sesame, sorghum, soybean, sugar beet, sunflower, sweet potato, triticale, wheat.

Cattle
  barley, brussel sprout, buckwheat, cabbage, carrots, cottonseed, forage grasses, forage legumes, kale, kohlrabi, linseed, maize, mangold beet, mustard, oat, parsnip, peanut, potato, rape, rice, rye, sorghum, soybean, sugar beet, sunflower, swede, turnip, wheat.

Sheep and goats
  barley, brussel sprout, buckwheat, cabbage, carrot, forage grasses, forage legumes, groundnut, kale, kohlrabi, linseed, maize, mangold, mustard, oat, potato, rape, rye, sorghum, soybean, sugar beet, swede, turnip, wheat.

According to another aspect, the present invention provides the use of an anti-parasitic protein against an animal parasite, which is preferably an inhibitor of an enzyme of the parasite, for example an inhibitor of a digestive enzyme of the animal parasite, for the manufacture of a composition suitable for administration to the host animal as a medicament or as a food for combating the parasite.

According to a further aspect the invention provides the use of a transgenic plant transformed with DNA encoding an anti-parasitic protein against an animal parasite, which is preferably an inhibitor of an enzyme of the parasite, for example an inhibitor of a digestive enzyme of the animal parasite, and capable of expressing the protein within the transgenic plant for the manufacture of a composition suitable for administration to the host animal as a medicament or a food for combating the animal parasite.

According to a still further aspect, the invention provides a composition adapted for oral, parenteral or topical administration to a host animal which comprises an anti-parasitic protein directed against a parasite to which the host animal is or may be subject, preferably an inhibitor of an enzyme of the parasite, the anti-parasitic protein having been expressed by a transgenic plant. The composition is preferably adapted for oral administration and may be in the form of a food for the host animal, or in the form of a drug or medicament.

According to another aspect, the present invention provides a composition adapted for oral, topical or parenteral administration to a host animal as a medicament or a food which comprises a cysteine protease inhibitor from maize or rice as an anti-parasitic protein.

The invention also provides a transgenic plant transformed with DNA encoding an anti-parasitic protein against an animal parasite in a form capable of expressing the protein within the transgenic plant, wherein the anti-parasitic protein is a cysteine protease inhibitor from maize or rice and the plant is a dietary crop for the host animal.

The animal parasite is preferably a helminth or a protozoan.

The parasite may be of the nematode genus Ascaridia or Ascaris.

For example the animal parasite may be a member of the Order Ascaridata including *Ascaris suum, Ascaris lumbricoides, Ascaridia gall,* Anisakis spp, *Parascaris eauorum, Toxocara canis, T. cati, T. vitulorum* and *Toxascaris leonina.*

The animal parasite may also be a trichostrongyle including *Nematodirus battus, Nematodirus spathiger, Nematodirus filicollis, Haemonchus contortus, Trichostrongylus colubriformis, T. tenuis, T. capricola, T. falcatus, T. rugatus, T. axei, Ostertagia ostertagi, O. circumcincta, C trifurcata, Oesophagostomum radiatum* and Cooperia cuticei.

The animal parasite may also be a strongyloid including *Strongyloides stercoralis, S. ransomi* and *S. papillosus.*

The animal parasite may also be a hookworm including *Necator americanis, Ancylostoma duodenale, A. ceylanicum, A braziliense, A. caninum* and Bunostomum spp.

The animal parasite may also be a metastrongyle including *Dictyocaulus viviparis, D filaria, D arnfieldi* and *Angiostrongylus cantonensis.*

The animal parasite may also belong to the Order Trichurata including *Trichuris trichuria, T. suis, T. ovis, Capillaria hepatica, C. annulata, C. caudinflata, Trichinella soiralis* and *T. psuedospiralis.*

The animal parasite may also be an oxyurid including *Heterakis gallinarum, Oxyuris equi, Enterobius vermicularis* and *E. gregorii.*

The animal parasite may also be a guinea worm including *Dracunculus medinensis.*

The animal parasite may also be a filarial worm including *Wuchereria bancrofti, Brugia malayi, Onchocerca vovulus, O. gutterosa, O. gibsoni, Loa loa, Dipetalonema perstans, D streptocerca, Mansonella ozzardi* and *Dirofilaria irmitis.*

The animal parasite may also be a tapeworm including *Taenia solium, T. saginata, Diphyllobothrium latum, Echinococcus granulosus, E. hydatigena, Hymenolepis diminuta* and *H. nana.*

The animal parasite may also be another helminth including *Schistosoma mansoni, S. haematobium, S. japonicum, S mekongi, S. matthei, S. intercalatum, S. bovis, Fasciola hepatica, F. gigantea, Fasciolopsis buski, Dicrocoelium dendriticum, Chlonorchis sinensis* and *Opisthorchis felineus.*

The animal parasite may also be a protozoan, including coccidia and amoeba.

For example the animal parasite may be a coccidian including *E.imeria acervulina, E. necatrix, E. maxima, E. brunetti, E. tenella, E. meleagrimitis, E. danailova, E. anseris, E. alabamensis, E. bovis, E. zuernii, E. ahsata, E. arloingi, E. debliecki, Isospora belli, Toxoplasma gondii, Sarcocystis hirsuta, S. porcifelis, S. cruzi, S. tenella, S. bertrami, S. fayeri, S. meischeriana, S. suihominis, S. hominis, S. gigantea, Besnoita bennetti, B. wallacei, Hammondia heydorni* and Cryptosporidium spp.

The animal parasite may also be an amoeba including *Entamoeba histolytica, E. hartmanni, E. gingivalis, E. coli, Endolimax nana, Naegleria fowleri* and *Iodamoeba buetschlii.*

The animal parasite may also be an intestinal flagellate including *Giardia intestinalis, Hexamita Rmeleagridis, Histomonas meleagridis, Trichomonas gallinarum, Spironucleus meleagridis* and *Dientamoeba fragilis.*

The animal parasite may also be another protozoan including *Trypanosoma brucei, T. brucei brucei, T. brucei* gambiense, *T. brucei rhodesiense, T. con golense, T. vivax, T cruzi, T. equiperdum, T. equinum, T. evansi, T. rangeli, T theileri, Leishmania tropica, L. tropica tropica, L. tropica major, L. aethiopica, L. donavani, L. donavani donavani, L donavani archibaldi, L. donavani infantum, L. donavani chagasi, L. mexicana, L. mexicana mexicana, L. mexicana amazonensis, L. mexicana pifanoi, L. mexicana aristedesi, L mexicana garnhami, L. braziliensis, L. braziliensis braziliensis, L. braziliensis guyanensis, L. braziliensis panamensis, L. peruviana, L. enriettii, L. hertigi, L. hertigi hertigi, L. hertigi deanei, L. aethiopica, Trichomonas vaginalis, T. tenax, T. foetus, Pentatrichomonas hominis, Plasmodium vivax, P. falciparum, P. ovale, P. malariae, P gallinaceum, Babesia bigemina, B. bovis, B. berbera, B divergens, B. argentina, B. major, B. caballi, B. equi, B. ovis, B motasi, B. traumanni, B. canis, B. gibsoni, B. felis, Theileria parva, T. annulata, T. mutans, T. hirei, T. sergenti, T hirci, T. ovis* and *Haematoxenus veliferous*.

The invention is based on the experimental work described in the following Examples. Part of this work is based on *Ascarida galli* which is a parasite of chicks. Whilst *Ascarida galli* itself is not of particular economic importance as a parasite, the related human and pig roundworms (*Ascaris uiumbricoides* and *Ascaris suum* respectively) are major world parasites. *A. galli* represents a suitable experimental model for the validation of the concept on which the present invention is based and demonstrates the applicablilty of this model to nematodes in particular and other animal parasites in general.

In the examples, reference is made to the accompanying drawings in which.

EXAMPLE 1

Figure 1:
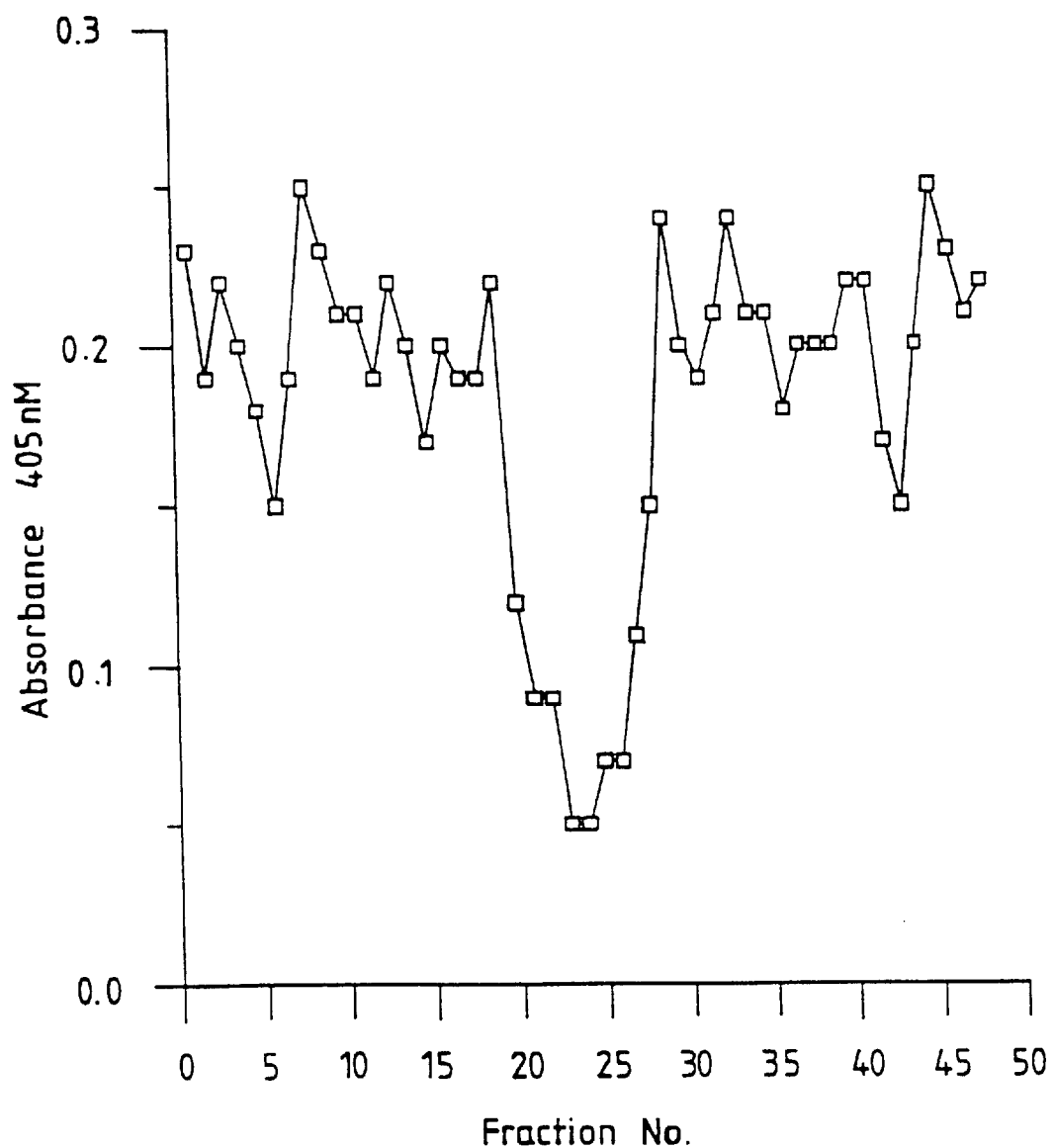
FIG. 1 shows papain proteolytic activity is inhibited by certain fractions of maize proteins eluted from CM-Sepharose.

Extraction of a cystatin from plants to demonstrate effects on parasites

Maize meal was stirred overnight at 40° C. in 50 mM Na acetate buffer (pH 5.0) and centrifuged for 30 min at 15,000 g. The supernatant was put on a CM Sepharose column (10×1 cm) equilibrated with acetate buffer (pH 5.0). The column was washed with acetate buffer and proteins eluted by a linear gradient system of NaCl (0–1M) in 50 mM Na acetate buffer (pH 5.0). 1 ml fractions were collected and tested for inhibition of papain using the papain-specific chromogenic substrate, p-Glu-Phe-Leu-p-nitroaniline.

The inhibition of papain was investigated by dissolving 0.5 mg/ml papain in 50 mM Tris-HCl at pH 7.5 and 100 μl placed in individual wells of a microtitre plate (NUNC) and incubated overnight at 4° C. After several rinses of the plates in phosphate buffered saline (PBS), papain coated to the plate was activated for 20 min with 0.1M 2-[N-morpholino] ethanesulphonate (MES—OH) pH6 containing 4 mM dithiothreitol (DTT) and 4 mM EDTA. These prepared plates were used for inhibition assays.

100 μl aliquots of the eluted zeacystatin preparation from CM Sephadex chromatography were added and incubated for 30 min at 37° C. The plates were rinsed thoroughly in PBS (10 mM $Na_2PO_4$/$KH_2PO_4$+0.14M NaCl) before 100 ml 50 mM p-Glu-Phe-Leu-p-nitroaniline in 50 mM MES—OH (pH 6) containing 2 mM DTT and 2 mM EDTA was added. The colour was allowed to develop before absorbance was measured at 405 nM using a microtitre plate reader (Biorad). Blanks consisted of wells without coated papain. The most active fractions (eluted between 0.2–0.3M NaCl) were pooled and dialysed extensively against 0.1M $KH_2PO_4$/$K_2HPO_4$ buffer (pH 7.0).

Maize inhibitor was purified by affinity chromatography using carboxymethylpapain-Sepharose made according to the method of Anastasi et al (1983). Pooled maize fractions were loaded onto the column previously equilibrated with phosphate buffer (pH 7.0), and the solution allowed to percolate. Unbound protein was removed by washing with 10 column volumes of phosphate buffer (pH 7.0). Inhibitor was eluted with 2 column volumes of 75 mM $K_3PO_4$ (pH 11.5) containing 0.1M NaCl and the 1.0 ml fractions quickly adjusted to pH 7.5 with 3M Na formate/formic acid buffer (pH 3.0) prior to dialysis against distilled water.

Figure 2:
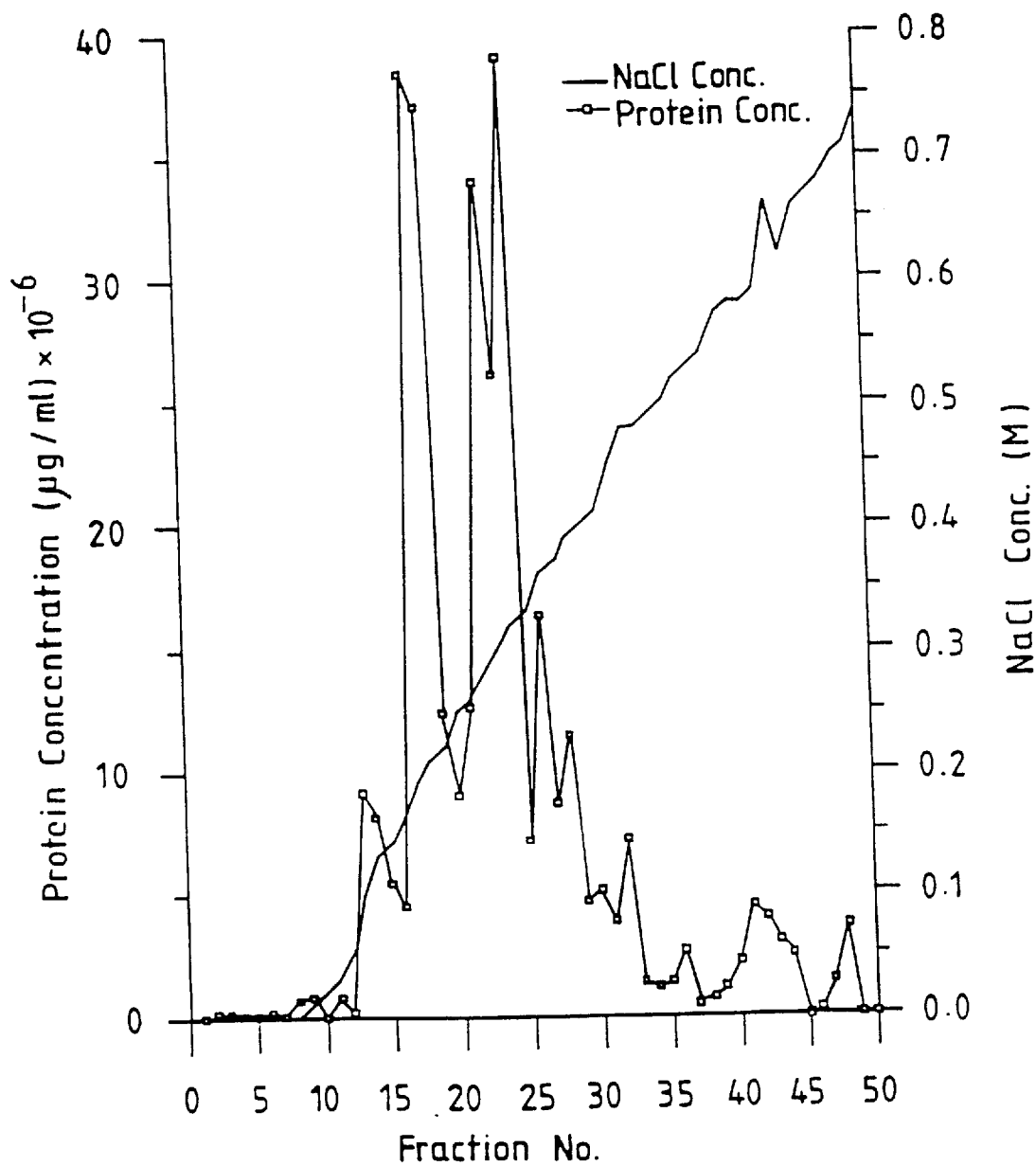
FIG. 2 shows maize proteins eluted from CM-Sephadex in a NaCl gradient.

FIG. 1 shows the effect of fractions on coated papain activity using p-Glu-Phe-Leu-p-nitroaniline as substrate. As shown by this figure, the fractionation of maize meal protein on CM Sepharose revealed major papain inhibitory properties between fractions 20–28 and a minor inhibition for fractions 42–44; the latter effect was not studied further. FIG. 2 shows the CM Sephadex C50 chromatography profile of acid-soluble maize proteins eluted with a linear gradient of NaCl. Fractions eluted in 0.2 to 0.4M NaCl were used to assay for protease inhibitors (Abe and Arai, 1985; Abe and Whittaker, 1988). This information was used to devise a larger-scale method for extracting sufficient material for subsequent experiments.

The protease inhibitor was extracted in bulk from maize meal (pollenta medium, Smith Flour Mills, Worksop, Notts., UK) using a batch technique. 5 kg of maize meal was extracted in 15 liters of 50 mM Na acetate buffer (pH 7.0) for 4 h at room temperature. The mixture was filtered through 4 layers of muslin, adjusted to pH 5 with acetic acid and left overnight at 4° C. The supernatant (about 9 liters) was siphoned into a container containing 3 liters of CM Sephadex previously equilibrated with 50 mM Na acetate buffer (pH 5.0) and the mixture gently agitated for 3 h at 4° C. The mixture was poured through a 30 μm mesh filter and the retained Sephadex washed extensively with 50 mM acetate buffer (pH 5.0). 1.5 liters of 50 mM acetate buffer (pH 5.0) were added and the mixture gently agitated for 3 h at 4° C. 1.5 liters of 50 mM acetate buffer (pH 5.0) containing 0.2M NaCl was added to the gel and allowed to equilibrate for 20 min with gentle agitation. The liquid was removed by filtration through 30 μm mesh and discarded.

The Sephadex was re-treated with 1.5 liters acetate buffer containing 0.4M NaCl and the supernatant (about 1.2 liters) containing eluted proteins was kept. Ammonium sulphate was added to 80% (w/v) and the precipitate collected by centrifugation at 10,000 g for 15 min, and re-suspended in 50 ml of distilled water. Salts were removed by dialysis against distilled water overnight at 4° C. The dialysed solution containing inhibitor was tested for activity with papain.

Figure 3:
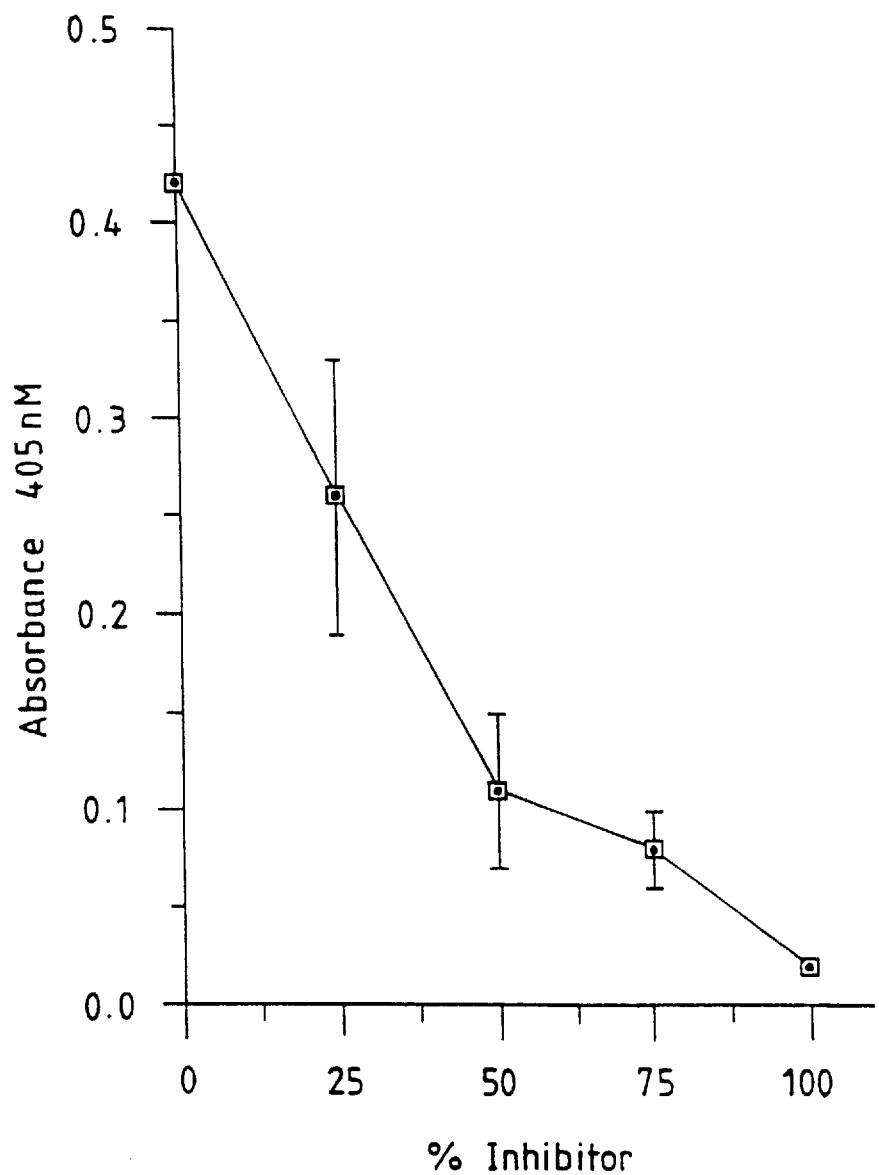
FIG. 3 shows inhibition of coloration due to papain activity by maize eluted proteins obtained by the bulk extraction method.

The final elutant between 0.2–0.4M NaCl from CM-Sephadex in this larger scale preparation was tested for potency against papain. For this test, 50 μl of 1.5 μg/ml papain was added to 50 μl of 62 μg/ml or 46.5 μg/ml or 31 μg/ml of the eluant protein for 20 minutes before addition of substrate. FIG. 3 shows the effect of partially purified inhibitor from maize (large scale batch method) on the activity of papain (100%=undiluted inhibitor; 0%=no inhibitor). Undiluted CM-Sephadex fraction contained 31 μg of inhibitor in 100 μl. From FIG. 3 it can be seen that undiluted CM-Sephadex extract almost completely blocked papain activity and 30% inhibition was obtained with 15.5 μg zeacystatin/100 μl (i.e. 25% in FIG. 3).

EXAMPLE 2

The protease activity of animal parasites

Ascaripain from *Ascaris suum* is similar to Ascaridia cysteine protease. Both prefer hydrolysis of Z-Phe-Arg-aminomethylcoumarin and both have limited action on Z-Phe-Arg-Arg-aminomethylcoumarin and Bz-Arg-aminomethylcoumarin. Both proteases are highly sensitive to egg white cystatin, E64 and zeacystatin and both are stimulated by EDTA/DTT. Pepstatin and serine protease inhibitors have no effect.

Cysteine proteases were extracted from whole *Ascaridia galli* obtained from the small intestine of chicks, snap frozen in liquid nitrogen and stored at −70° C. until required. 4 g of frozen worms were homogenised in 40 ml of 30 mM Tris-HCl (pH 7.5) buffer (TB), centrifuged at 20,000 g for 30 minutes at 4° C. and the resultant supernatant mixed with 5 ml Q-Sepharose (fast flow) previously equilibrated with TB. The mixture was gently stirred overnight at 4° C. and the matrix poured into a 10×1 cm column and allowed to drain. The gel was washed with 15 column volumes of TB with a flow rate of 1 ml min$^{-1}$. Proteins were eluted with a 0–1M NaCl gradient in TB. 1 ml fractions were collected and assayed for cysteine protease activity with the specific fluorogenic substrate Z-Phe-Arg-aminomethylcoumarin (Z-Phe-Arg-AMC; Sigma).

A 50 μl sub-sample of each fraction from column chromatography was added to 50 μl of 0.1M MES—OH (pH 6.0) containing 2 mM EDTA and 2 mM DTT (MED) and 50M of Z-Phe-Arg-AMC (first dissolved in DMSO). The solutions were mixed and placed in wells of a 96 well microtitre plate (NUNC) and viewed under UV light after 30 min incubation at 37° C.

Wells of the microtitre plate with a fluorescent product signified presence of proteolytic activity in the corresponding fraction from which the 50 μl sub-sample was derived. The main fractions giving rise to the principal fluorescence were pooled, dialysed against MED buffer and used for inhibition studies. Protein concentration was assayed according to Bradford (1974).

60 μl of dialysed pooled cysteine protease fraction derived from *A. galli* was added to (i) 30 μl of distilled water (ii) 10 μM E64 or (iii) 30 μM zeacystatin and pre-incubated for 20 min at 37° C. 50 AM of Z-Arg-Phe-β-naphthylamine was added and the reaction terminated after 20 min with 100 μl of Fast Garnett reagent containing Mersalyl acid and Brij 35 (Barrett and Kirschke, 1981). The resultant optical density due to protease activity was measured at 490 nm using a micotitre plate reader (Biorad).

Figure 4:
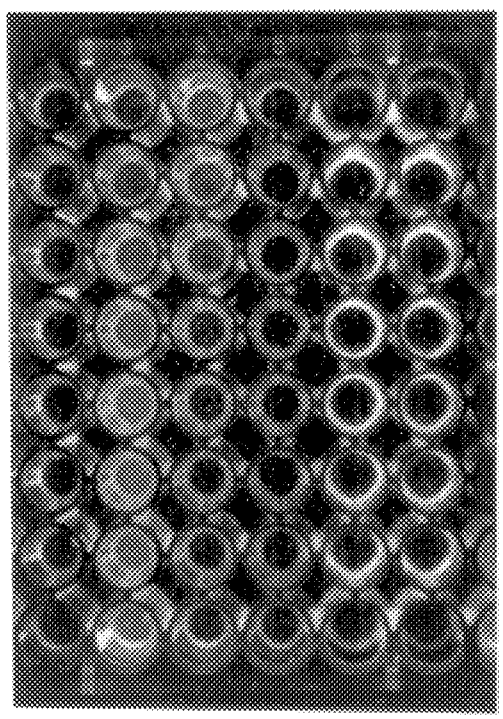
FIG. 4 shows fluorescence caused by cysteine proteinase activity of *Ascaridia galli* in fractions of a worm homogenate passed down a Q-Sepharose ion-exchange column.
Figure 5:
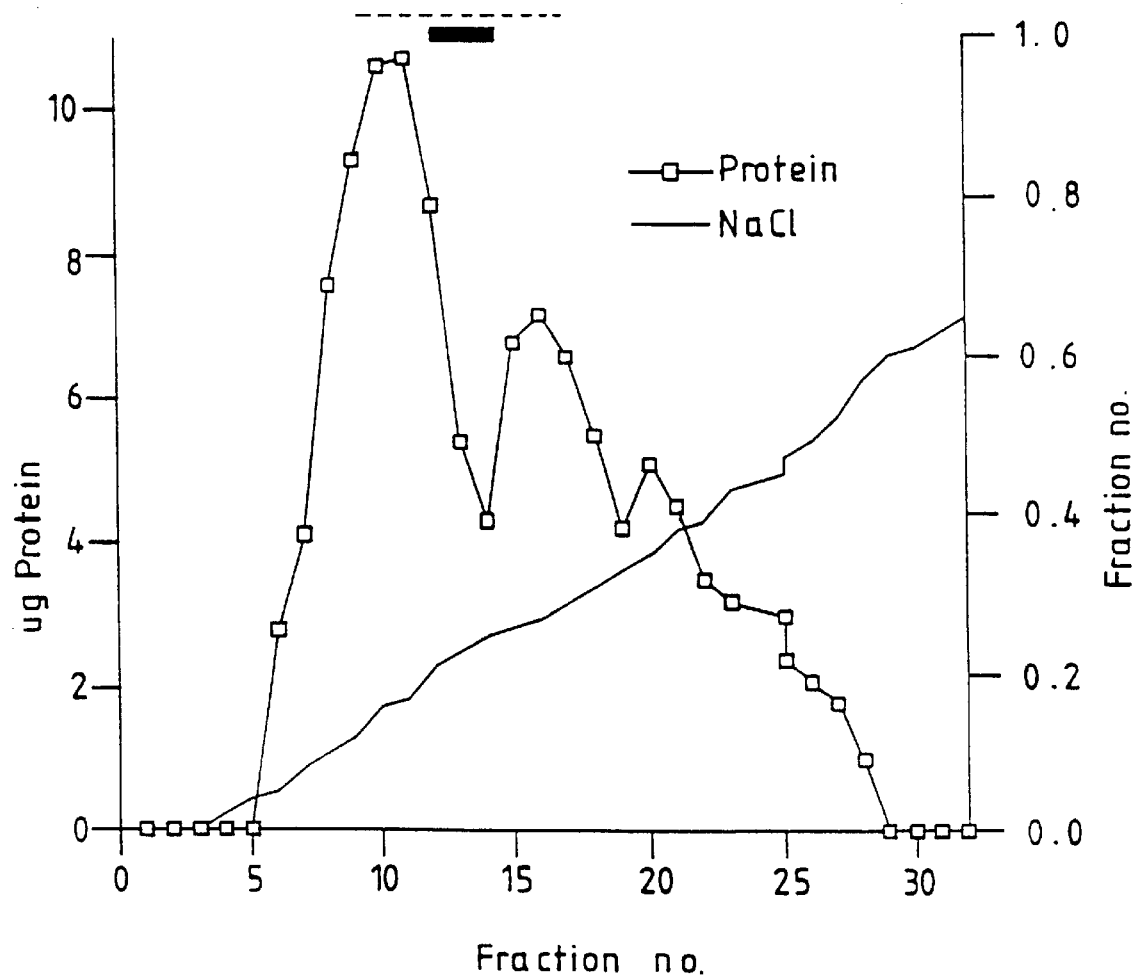
FIG. 5 shows protein content of *A. galli* fractions used in FIG. 4.

Proteolytic activity of eluted worm fractions from Q-Sepharose chromatography was monitored in a microtitre plate with Z-Phe-Arg-AMC. FIG. 4 shows fluoresence of fractions viewed with UV light from Q Sepharose chromatography after incubating with Z-Phe-Arg-AMC. Fluorescence in wells indicates proteolytic activity (cathepsin L-like enzymes). Cysteine proteases were detected between fractions 9–19, with peak proteolytic activity found between fractions 12–15. FIG. 5 shows protein content (indicated by the solid line with square symbols) of fractions obtained from Q-Sepharose ion-exchange chromatography. The dashed line represents proteolytic activity in fractions 9 to 19 with peak activity found in fractions 12 to 15 (thick line). The solid line without symbols indicates NaCl levels of the eluant. The activity corresponded with the second peak of eluted protein which came off at 0.23–0.28M in the NaCl gradient. The most active fractions were pooled, dialysed against MES—OH (pH 6.0) buffer containing DTT and EDTA and assayed with E64 or zeacystatin. A single band of about 13 KDa was visualised after SDS-PAGE. and staining for protein with Commassie Blue.

Figure 6:
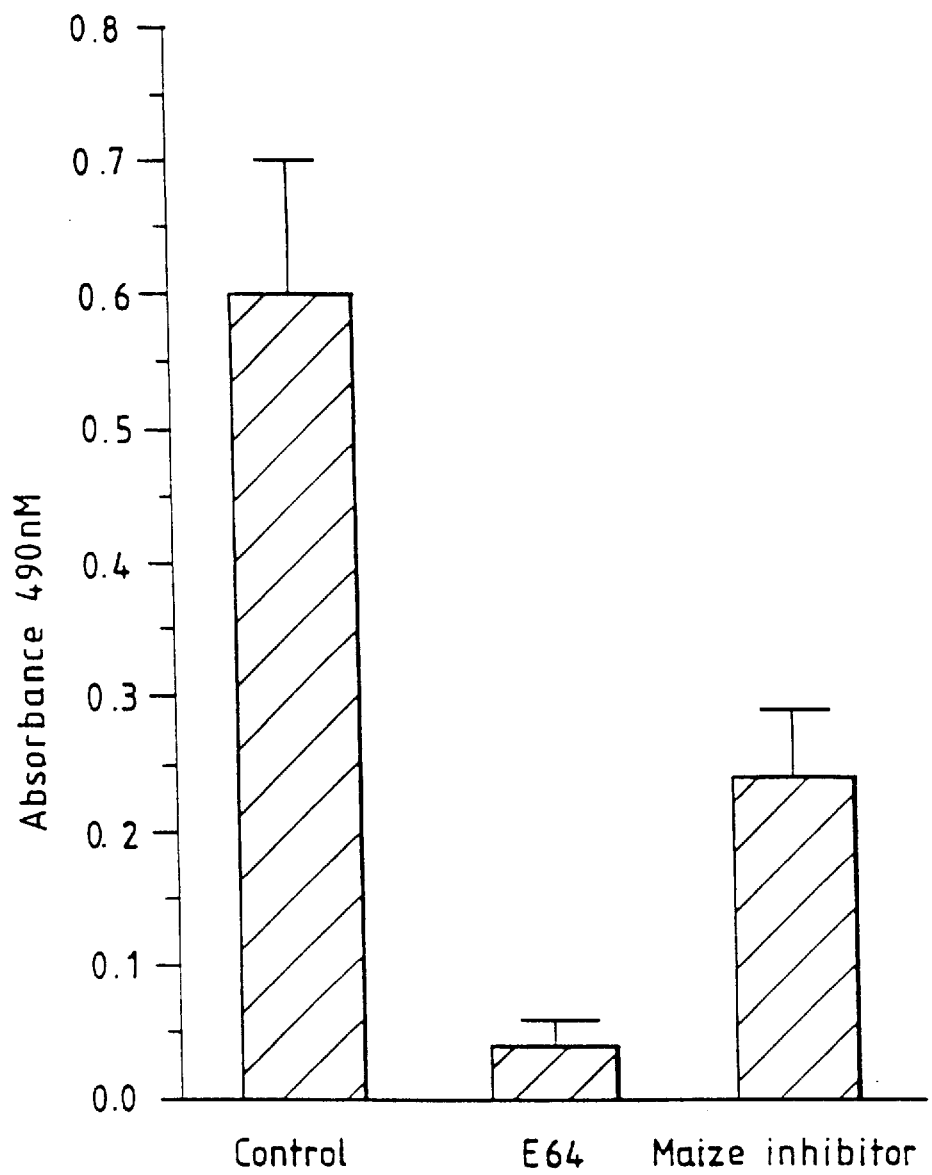
FIG. 6 shows the effect of no inhibitor, E64 and the maize inhibitor preparation on proteolytic activity of *A. galli*.

FIG. 6 shows the effect of inhibitors on the activity of protease from *Ascaridia galli*. Controls containing no inhibitor indicate a relative activity of 100% towards Z-Phe-Arg-β-napthylamine and is represented by an absorbance of 0.6 OD units. E64 inhibited proteolytic activity by over 90%, whilst the zeacystatin curtailed proteolysis by 65%. A single band of about 13 KDa was seen on SDS-PAGE as before.

The use of a cysteine protease-specific substrate, together with inhibition of the enzyme by E64, confirms the presence of cysteine proteases in *A. galli* with properties not dissimilar to those of cathepsin L from a range of parasitic organisms and Ascaripain from *A. suum* (Koritsas, unpublished).

EXAMPLE 3

Test to show protease inhibitors can withstand physiological conditions occuring in the alimentary system of livestock and humans.

Figure 7:
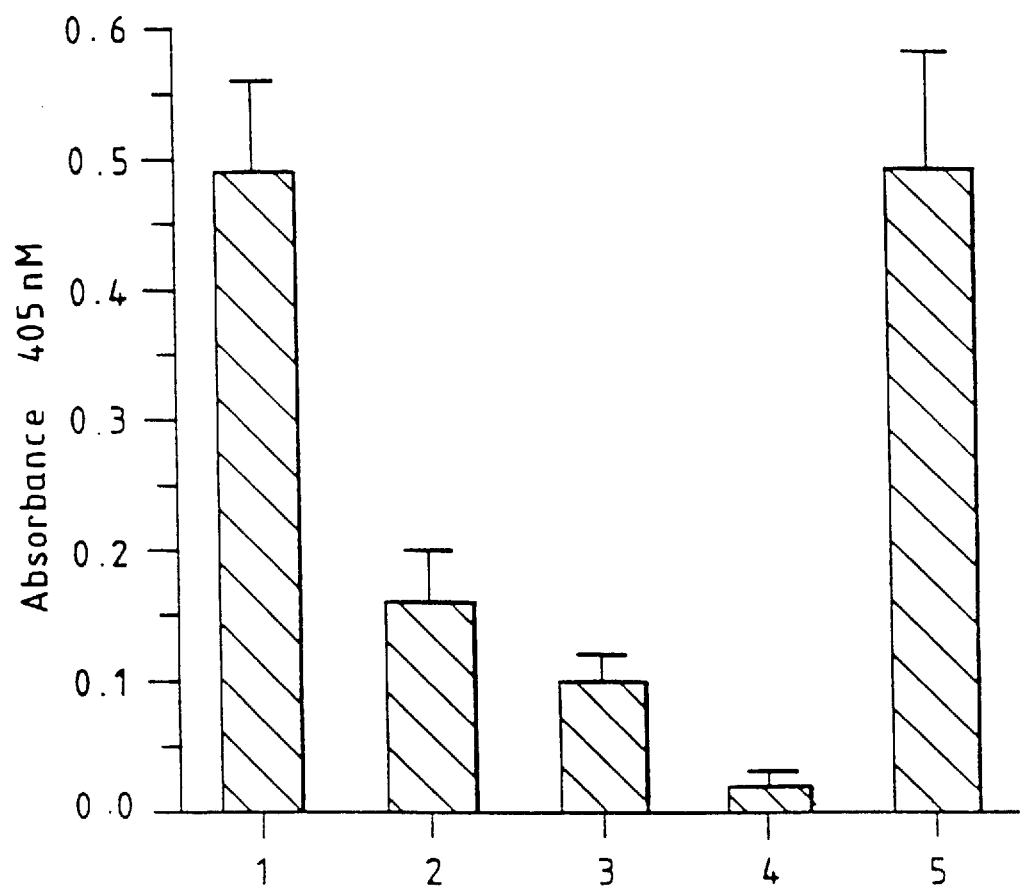
FIG. 7 shows the influence of pre-treatment of maize inhibitory digestive enzymes and pH condition of the mammalian digestive system on its ability to inhibit papain.

The orally administered protective agent must retain its efficacy after passage through the alimentary system to its site of action against the parasite. An experiment was therefore carried out to demonstrate that certain protease inhibitors are capable of retaining their efficacy after exposure to the enzymes that digest proteins in the mammalian alimentary system. FIG. 7 shows the action of "gut-enzyme-treated" maize inhibitor on the activity of papain. Absorbance of 0.49 represents 100% papain activity. In FIG. 7, 1=papain only, 2=papain+untreated inhibitor, 3=papain+enzyme-treated inhibitor; 4=buffer only+treated inhibitor; 5=papain+enzyme mixture only. The example shows the ability of zeacystatin to withstand challenge by proteolytic enzymes of the stomach in a highly acidic environment and then to withstand hydrolytic enzymes found in the more alkaline pHs of the intestine.

50 μl of 0.1 mg/ml zeacystatin was mixed with 25 μl pepsin (2 μl/ml) for 90 minutes at pH 2.0 (37° C.) before being inactivated by increasing the pH to 8.0 with 3M NaOH. 25 ml of an enzyme cocktail containing 5 mg/ml of each of trypsin, chymotrypsin and elastase in 50 mM Tris-HCl (pH 8.0), 2 mM CaCl$_2$ was then added and incubated further at 37° C. for 90 min. The enzymes were inactivated by bringing down the pH to 1.5 with 1M HCl and left for 30 min at 4° C. The mixture was centrifuged and the supernatant brought to pH 6.0 with NaOH.

Zeacystatin was assayed for inhibition with papain at a 1:1 molar ratio in buffer (pH 6.0) containing 2 mM DTT and 4 mM EDTA. The inhibitor and enzyme were preincubated for 15 min at 37° C. prior to addition of papain substrate (50 μm p-Glu-Phe-Leu p-nitroaniline) and incubated for a further 30 min. Controls were treated similarily but zeacystatin was not added at the start of the reaction. Absorbance was read at 405 nm as before.

No apparent effect was seen on inhibitor activity which remained very effective in reducing papain activity.

EXAMPLE 4

Evidence for the effect of protease inhibitors on animal parasitic nematodes held in vitro 35 day old Ascaridia were removed from the host and thoroughly rinsed with 0.9% (w/v) NaCl in distilled water before transfer to 3 cm plastic Petri-dishes containing basic culture medium: $CaCl_2$ $2H_2O$ (0.24 mg/ml), $Na_2HCO$, (0.2 mg/ml), NaCl (9.0 mg/ml) and D-glucose. (1 mg/ml). Streptomycin sulphate (100 mg) and penicillin (60 u) were included to reduce microbial contamination.

Three treatments of five replicates containing 4 worms each were used to assess the potency, of the maize inhibitor. Each treatment was carried out in the basal culture medium supplemented with:

(i) 0.5 mg/ml bovine serum albumin (BSA);
(ii) 0.5 mg/ml maize protein recovered by the batch method of which zeacystatin was estimated to be at 22 μg/ml;
(iii) no supplement to the medium.

The worms were kept for 4 days in the dark at 37° C. and solutions changed daily. Zeacystatin concentration was estimated using a papain inhibition assay as previously and by comparison of the inhibition derived from the batch method with that achieved for the zeacystatin obtained by affinity chromatography earlier.

Worms cultured in basic medium and that supplemented with BSA remained active for 4 days at 37° C. Most worms in the maize proteins enriched for the inhibitor were dead but a few were inactive but responsive to a tactile stimulus. These observations were quantified and expressed as activity scores for each individual on the following limited scale: 0 (dead), 1 (inactive but responsive to a tactile stimulus), 2 (intermittent activity) to 3 (frequently active). The results are presented in Table 1 which shows a clear effect of the preparation containing zeacystatin on the viability of the nematodes in vitro.

TABLE 1

Effect of Maize inhibitor after 4 days on the activity and general appearance of A. galli maintained in basic medium in the dark at 37° C.

|  | No Inhibitor | Inhibitor | BSA |
| --- | --- | --- | --- |
| Activity Score | 3.00 ± 0 | 0.85 ± 0.65 | 2.75 ± 0.35 |

Figure 8:
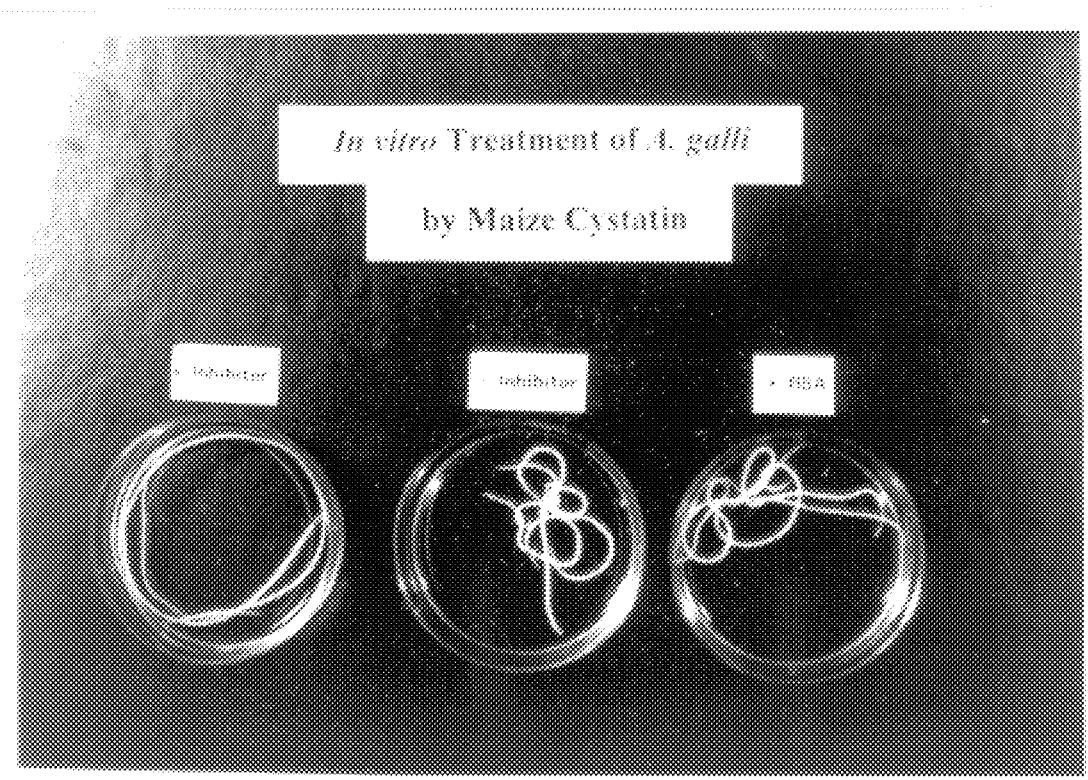
FIG. 8 shows the effect of maize inhibitor on *A. galli* incubated in vitro for 4 days at 37° C. in the dark.

FIG. 8 shows the general appearance of A. galli after 4 days treatment with inhibitor and BSA in the dark at 37° C.

This work establishes that maize meal contains an inhibitor capable of affecting the well-being of whole worms in culture. This finding establishes that a preparation of maize proteins enriched for zeacystatin is capable of inducing lethargus leading to mortality in A. galli.

EXAMPLE 5

Evidence for in vivo effect of protease inhibitors on animal parasitic nematodes within hosts Two-week old chicks were paired according to their body weight and housed in eleven cages each containing two birds on concrete floors covered with wood shavings at 15°–22° C. Food and water were available ad libitum. Two days prior to infection of the chicks with A. galli, the birds were injected (and every 10 days thereafter) in the thigh with an immunosuppresant, (Depo-medrone-Upjohn). This was necessary to ensure a high worm burden in the chicks.

Birds were weighed and each was inoculated orally with 100 embryonated eggs of A. galli in 0.1 ml distilled water. Three days after infection, one chick from each cage was dosed orally with 0.5 ml water from a syringe and the other treated similarily with 1 mg of the batch isolated maize proteins containing 22 μg zeacystatin in 0.5 ml water. The dose was given daily until one day before sacrifice of the birds. Birds were weighed, sacrificed and the worm burden removed from the small intestine. The nematodes were rinsed with water and placed in fixing solution containing 2 ml triethanolamine, 7 ml formalin (40% formaldehyde) and 91 ml distilled water.

Parasite length and width were determined by placing the animals on a graticule overlayed with acetate sheeting. They were viewed under a stereobinocular microscope with reflective lighting and their length and maximum width recorded. Measurements of the reproductive systems of females were made as an indicator of reproductive development. Reproductive structures were gently removed with dissecting needles, placed on acetate and the length of the female reproductive system recorded. The ratio of the female reproductive structures to worm length was calculated.

Figure 9:
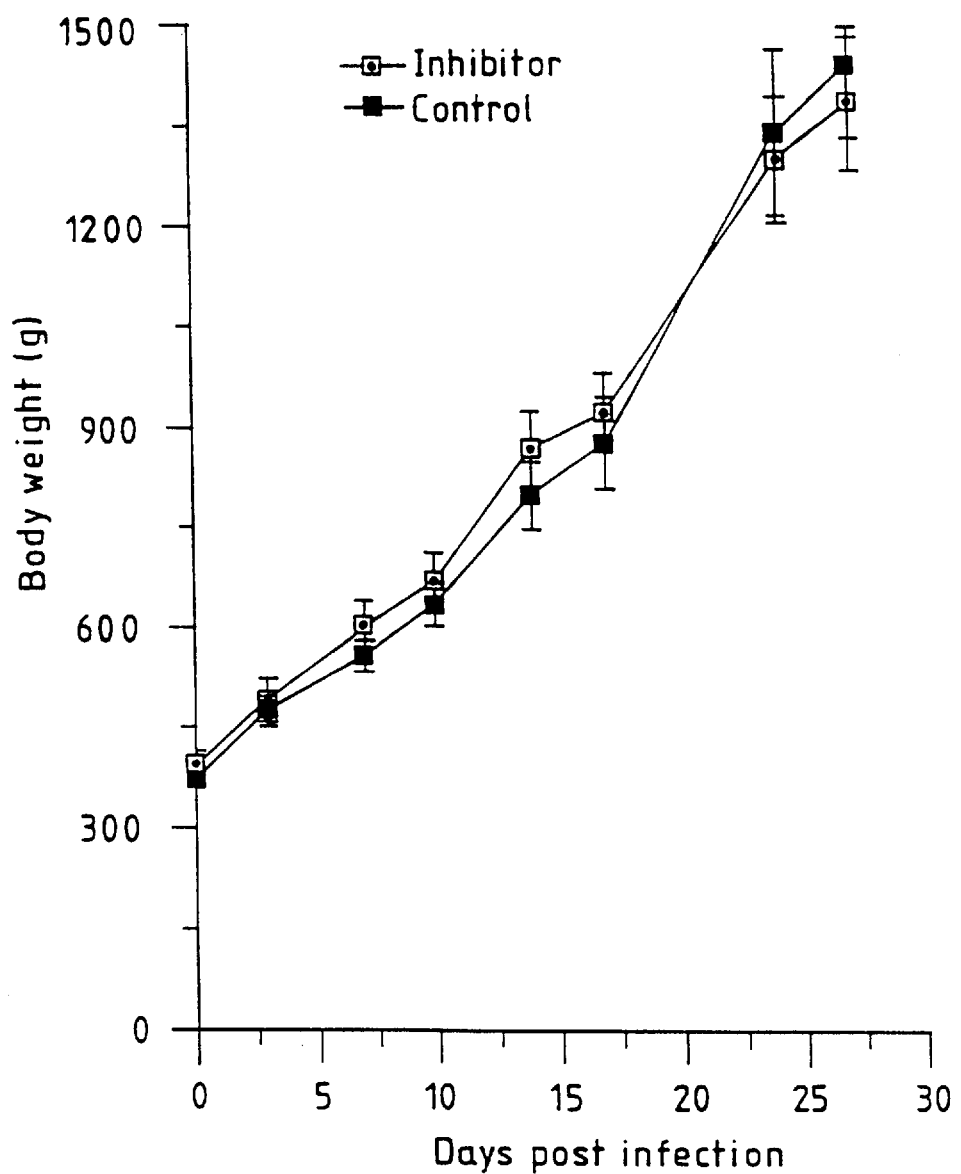
FIG. 9 shows no effect of maize inhibitor on growth rates of chicks.

FIG. 9 shows the effect of maize inhibitor on the growth rate of chicks. Birds fed, on maize inhibitor showed no ill effects and continued to grow at the same rate as the controls. The feeding behaviour and water uptake of both groups showed no differences. All three measurements on parasite body length, width and volume revealed significant reductions (Table 2). The inhibitor reduced worm length, width and volume, by 10, 13 and 32% respectively. Values were estimated from measurements of length and maximum width using a standard formula (Andrassy, 1956).

TABLE 2

The effect of partially purified inhibitor on the size of A. galli growing in chicks after 28 days treatment. Values represent means ± sd of over 100 replicates

| Parameter | Control | Inhibitor | Significance |
| --- | --- | --- | --- |
| Length (mm) | 51 ± 2.5 | 46 ± 1.5 | P <0.001 |
| Width (mm) | 0.83 ± 0.04 | 0.72 ± 0.02 | P <0.05 |
| Volume (mm$^3$) | 20.67 ± 1.2 | 14.03 ± 0.07 | P <0.001 |

The length of the ovaries housing the developing eggs was highly significantly reduced (P<0.001) in worms from chicks treated with zeacystatin (Table 3). Even when taking body length into account, the effect was still highly significant both in absolute lengths and as a ratio to body length.

TABLE 3

Effect of partially purified inhibitor on the reproductive structures of *A. galli* after 28 days treatment of chicks. Values represent means ± sd of 24 replicates

|  | Control | Inhibitor | Significance |
| --- | --- | --- | --- |
| Uterus (mm) | 67.0 ± 7.0 | 41.0 ± 18.4 | P <0.001 |
| Uterus: female Body length | 1.25 ± 0.12 | 0.81 ± 0.33 | P <0.001 |

This work demonstrates that normal growth and development of *A. galli* was affected by the uptake of zeacystatin by the host. This requires the inhibitor to remain active after oral administration and to be taken up by the parasite within the intestine. This uptake in the experimental system is sufficient to have effect on the growth and development of the parasite. Therefore the effects established in examples 1–3 are substantiated with the results in example 4.

The suppression of growth of *A. galli* was achieved with necessarily low levels of zeacystatin because of the need to recover the inhibitor from a low concentration within maize meal. The clear effect were achieved with doses of only 22 µg/day of zeacystatin. This is a small fraction of that available via the diet given expression levels of 1–2% total soluble protein is often achieved for transgenes in plants including a protease inhibitor (Hepher & Atkinson, 1992). Such levels could be delivered in as little as 11–22 mg of dry food/day. This is only 0.005–0.05% of the daily food intake of the birds and gives scope for considerable increase in the daily dose rate once the inhibitor is expressed in experimental transgenic plants with a constitutive promoter such as Cauliflower mosaic virus 35S promoter.

EXAMPLE 6

Extraction of cloned cystatin and evidence for an in vitro effect on animal parasitic protozoa in culture Preparation and manipulation of DNA Plasmid DNA was purified from *E. coli* cultures by the alkaline lysis method (Sambrook et al., 1989). Restriction digests and ligation reactions were carried out using the recommendations of the manufacturer of the relevant enzymes. DNA fragments were recovered from agarose gels using an electroelution chamber (IBI) following the manufacturer s protocol. Oligonucleotides were synthesised on an Applied Biosystems 381A instrument. DNA sequencing of double stranded plasmid DNA was performed using Sequenase version 2.0 (Amersham), according to the manufacturers instructions.

Cloning of the cystatin

Oc-I was amplified from genomic DNA of *Oryza sativa L. japonica* with primers P1 and P 2 designed from published sequence data (Abe et al, 1987) and with the addition of restriction enzyme sites to assist cloning.

The intron was removed using the PCR technique of SOEing (Horton et al 1989) using primers P1/P3 and P2/P4 to amplify the two exons. These were then SOEn together by amplifying with primers P1 and P4. The SOEn product was cloned into SmaI/EcoRI pBluescript. The sequence of the cloned coding region was verified by comparing with the published data for Oc-I (Abe et al 1987).

The sequences of primers P1 to P4 are shown as follows:
Primer P1 SEQ ID NO. 1
Primer P2 SEQ ID NO. 2
Primer P3 SEQ ID NO. 3
Primer P4 SEQ ID NO. 4

Expression of Oc-I

Oc-I expressed from pQE30 (QIAexpress system) contained six N-terminal histidine residues, encoded by the vector to allow one-step Nickel chelate affinity. Oc-I protein was purified from 1 liter cultures of *E. coli* M15[pREP4] harbouring the pQE30 derived expression plasmid. 20 ml overnight cultures were used to inoculate 1 liter of LB media and grown at 37° C. to $A_{600}$ 0.7–0.9. IPTG was added to a final concentration of 2 mM and growth was allowed to continue for a further 2 h. The cells were harvested by centrifugation at 10,000 g for 10 min. The cells were resuspended in a total volume of approximately 12 ml of sonication buffer (50 mM $Na_2HPO_4$, 300 mM NaCl) and stored at −20° C. overnight. The sample was thawed and aliquoted to three 15 ml tubes and sonicated on ice in short pulses (3×30 sec). Cell debris was pelleted by centrifugation (10,000 g) and approximately 0.5–0.75 ml of Ni-NTA resin slurry (Qiagen, Calif., USA) was added to each tube and mixed gently on ice for 1 h. The resin was collected (1000 g for 1 min) and washed with 5 ml of buffer (50 mM $Na_2HPO_4$ pH 6.0, 500 mM NaCl, 40 mM imidazole at 4C for 0.5 h). Protein was eluted with 1 ml of elution buffer (50 mM $Na_2HPO_4$, 300 mM NaCl, 100 mM EDTA) and the resin was re-pelleted at 1000 g for 1 min and the elution repeated a further two times. The purified proteins were analysed by SDS-PAGE (Hames 1981) and only one protein was detected on these gels (Commassie staining) and following Western blotting using the polyclonal antibody prepared against this protein (see below).

Antibody production

Oc-I antibodies were raised in male Wistar rats (6 weeks old) which were immunised intraperitoneally. Three injections were given at four week intervals of 100 µg Oc-I recovered from the pQE30 expression system in a final volume of 300 µl. The first injection was an emulsion of protein and complete Freund s adjuvant in a 1:1 (v/v) ratio and the second and third injection were similar but used incomplete Freund s adjuvant. Ten days after the final injection, blood was collected and allowed to coagulate at 4° C. before centrifugation at 5000 g for 10 min. The resultant serum was collected and stored at −20° C. in glycerol. The antibody gave optimal results in ELISA at a dilution of 1 in 10000 and recognised both native and denatured protein.

Tachyzoites of *T. gondii* were produced by intraperitoneal passage in Tuck's Number 1 outbred mice, approximately $10^7$ parasites are injected intra-peritoneally and parasites for culture were harvested three days later by peritoneal lavage with F12 medium and used immediately.

MDBK cells were plated onto 13 mm cover-slip cultures at a density of $1×10^5$ per cover slip and incubated overnight in HAM's F12 medium (GIBCO) plus 10% foetal calf serum at 37° C. Tachyzoites of RH strain *Toxoplasma gondii* ($2×10^6$) were loaded onto each cover slip and incubated for 4 hours at 37° C. to allow invasion of the DBK cells. Cultures were then washed with F12 medium to remove extracellular parasites and the inhibitor was added at a concentration of 0, 30 or 120 µg/ml. The cultures were incubated for a further 24 hours at 37° C. and then removed, washed with PBS, fixed with Bouin's solution and stained with Geimsa. Parasite growth was assessed by scoring approximately 200 cells for the number of infected cells and the total number of parasites in the sample.

The percentage of MDBK cells infected with *T. gondii* fell from 76±9 in the control to 66±2 and 59±0.6 with increasing concentration of inhibitor. The number of *T. gondii* was 4.2±0.17 per host cell when an inhibitor concentration of 120 g/ml was used. This was a significant reduction (P<0.05

Analysis of variance, linear combination, Snedecor and Cochrane, 1989) in the number of *T. gondii* per host cell compared with a lower concentration of 30 μg/ml of the inhibitor and the control respectively (see Table 4 below).

TABLE 4

|  | % cells infected | number parasites/cell |
|---|---|---|
| Control (no inhibitor) | 76 ± 9 | 5.8 ± 0.83 |
| Inhibitor treated 30 μg/ml | 66 ± 2 | 6.3 ± 0.63 |
| Inhibitor treated 120 μ/ml | 59 ± 0.6 | 4.2 ± 0.17 |

EXAMPLE 7

Anti-nematode effect of cystatin when ingested by a nematode

Cysteine proteinases have been reported from animal parasitic nematodes (Sakanari, 1990; Healer et al 1991; Cox et al 1990; Pratt et al 1990) but feeding trials are not readily carried out using obligate parasites. In situ hybridisation has demonstrated transcripts of cysteine proteinases are abundant in the intestine of the bacterial feeding nematode, *Caenorhabditis elegans* (Ray and McKerrow, 1992). This animal can be fed and reared on *E. coli* on media to which proteins of interest can be added. Therefore we have used this system to gain insights into the probable mode of activity of a cystatin against nematodes. This work involve cloning a previously described cystatin from rice (Abe et al 1987) and expressing it in a bacterial expression vector. The expressed protein was recovered and used to add to the agar from which *E. coli* fed.

Challenging *C. elegans* with a cystatin

*Caenorhabditis elegans* was cultured on NGM agar carrying a lawn of OP50 *E. coli* as described by Wood (1988). Populations were maintained for 5 days after which time an agar plug from the colony plate was inserted onto fresh media. When required, the Oc-I (see Example 6) or BSA was added to the cooled medium to a final concentration of 2.5 mg $1^{-1}$ just before polymerisation. Single nematodes were transferred from non-supplemented solid agar plates to plates containing Oc-I or BSA.

In vivo testing against *C. elegans*

Feeding trials were set-up using *C. elegans* to examine the effect of Oc-I on nematode survival and growth. As soon as hermaphrodites became apparent on normal agar they were transferred to individual plates containing either Oc-I or BSA and egg laying was observed. Ten replicates were carried out for each condition. Irrespective of the culture conditions the hermaphrodites laid a mean of 300 eggs. Greater than 95% of the eggs hatched even when a cystatin was present in the medium. Of the larvae hatched from eggs on BSA, and Oc-I supplemented media and then transferred to normal media, 96.0%, and 97.0% completed development. Of the larvae hatched and left to develop on cystatin-supplemented media less than 2% of the larvae achieved normal development to adulthood, in contrast to 95% of corresponding larvae exposed to BSA-supplemented media.

Subsequently the larvae hatched under normal conditions were removed to media supplemented with either Oc-I or BSA. 50 larvae were removed at 6 h, 12 h, 24 h and 30 h (corresponding to the four larval stages L1, L2, L3 and L4 respectively). Of the larvae transferred 6, 12 or 24 h after hatching (on normal media) to media supplemented with Oc-I, none developed further to reach the mature adult stages. 76% of larvae allowed to develop on normal media for 30 h after hatching prior to transfer to Oc-I supplemented media carried on their development and reached adult male or hermaphrodite stages. The remainder of these larvae (24%) did not reach the adult stages of development. All juveniles hatched from eggs laid on media containing BSA and transferred to normal media developed into adult nematodes.

Figure 10:
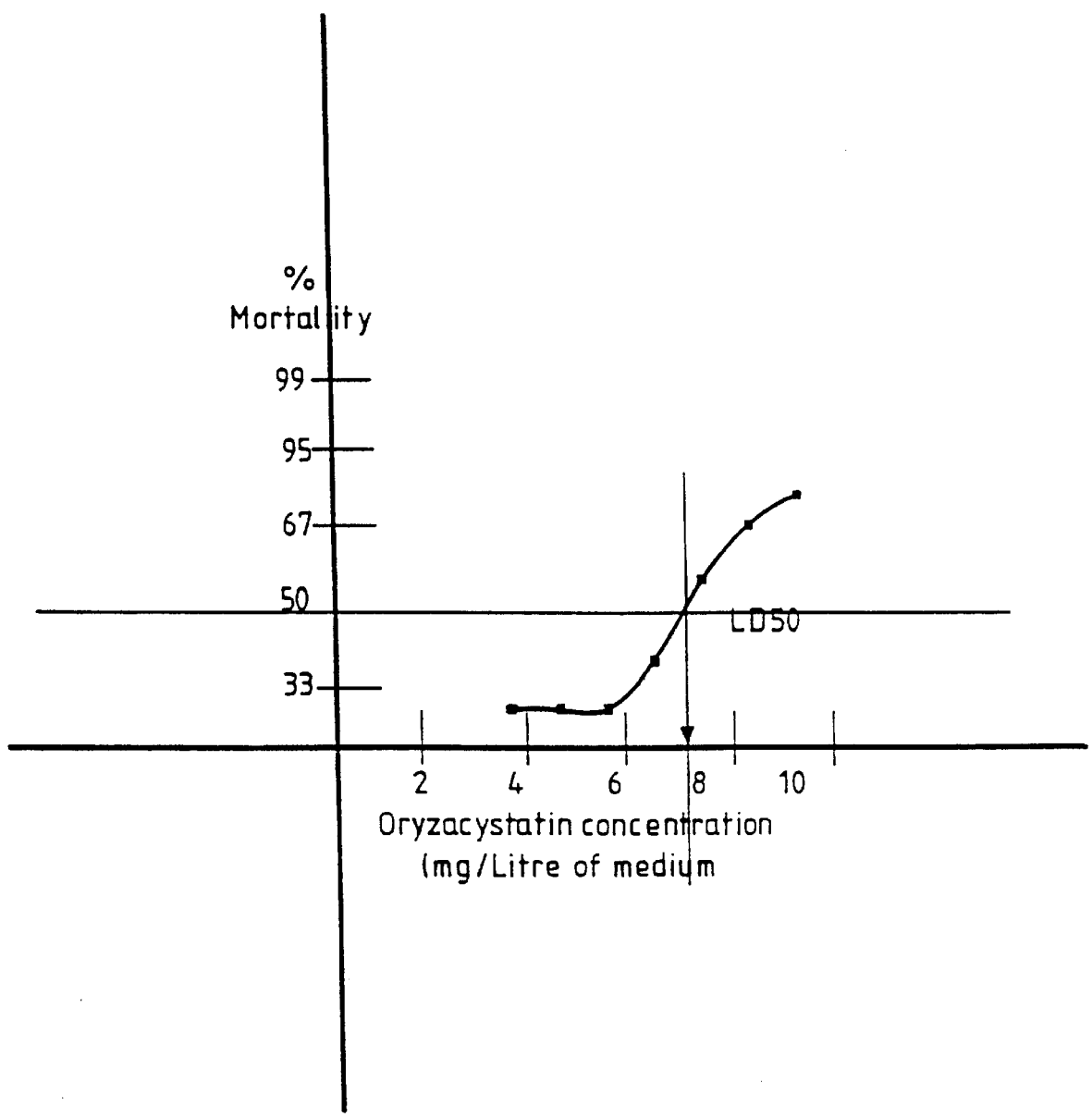
FIG. 10 shows a probit curve relating to the mortality of larvae of *C. elegans* to the oryzacystatin concentration in the medium from which it feeds.

Larvae of *C. elegans* were transferred to agar plates with *E. coli* in which the medium was supplemented with 0–10 mg/L of Oc-I and the subsequent mortality of the animals during feeding was estimated from activity of the animals. The data was subject to probit analysis from which a value for LD50 was derived of approximately 7 mg OcI per liter of medium. FIG. 10 shows a probit curve relating the mortality of larvae of *C. elegans* to the oryzactstatin concentration in the medium from which it feeds.

Some *C. elegans* larvae which failed to develop on Oc-I plates were transferred to fresh media not supplemented with the cystatin and observed for signs of recovery. The larvae failed to respond to the fresh food source and showed no signs of further development. These larvae also failed to respond to being touched, exhibiting no signs of movement following repeated stimuli indicating mortality and not dauer larvae formation.

These experiments established that a cystatin was only lethal to the nematode when actively feeding and growing. It did not prevent hatching or kill adult nematodes. The latter have completed the period of rapid growth that precedes sexual maturity. They may have sufficient endogenous reserves to ensure that further dietary intake of protein is not essential for their survival. Alternatively, the adult may have other than a cysteine proteinase in its intestine. Given the known presence of a cysteine proteinase in the intestine of larvae and the correlation between anti-parasitic effects of a cystatin and feeding, it seems likely that it is the intestinal digestion of protein that is disrupted in *A. galli* by a cystatin in other examples given in this application.

EXAMPLE 8

Anti-parasitic effect of a cystatin when expressed in plant material that is fed to the host These experiments used Oc-I to produce transgenic Arabidopsis expressing the cystatin constitutively. The fresh plant material was then used as supplement in the food of chicks that had been previously infected with *A. galli*. The objective was to confirm that a cystatin had the beneficial anti-parasitic effect already established by oral dosing in aqueous media when administered within the food of the host.

Transgenic Arabidopsis

Oc-I was cloned from within pBluescript into the vector pBIN19 (Bevan, 1984) using standard procedures (Maniatis et al., 1982) to produce a chimeric gene construct under control of the Cauliflower Mosaic Virus 35S promoter (Guilley et al., 1982). This promoter is generally constitutively active in plant tissues (Odell et al., 1985). Gene constructs for transformation were transferred to *Agrobacterium tumefaciens* by electro-transformation (Wen-Jun and Forde, 1989). Root explants of *Arabidopsis thaliana* ecotype C24 were transformed essentially as described by Valvekens et al. (1988) with modifications to the procedure as described by Clarke et al. (1992). Aseptically grown roots were excised and pre-incubated for 2–3 days on an agar-solidified medium containing plant growth regulators for callus-induction before being cut into approximately 0.5 cm explants and inoculated with Agrobacterium. Following 2 days of co-cultivation with the bacteria, explants were transferred to shoot-inducing medium and after 10–14 days transformed plants began to regenerate. Regenerated plants were individually transferred to plant growth regulator-free medium and allowed to set seed in vitro. The resulting seeds were used to bulk up stocks and the subsequent generation used for feeding experiments. Seeds were sown in standard seed trays and grown under glasshouse conditions. Seeds of non-transformed Arabidopsis were similarly sown. Chicks were supplied with rooted, intact, fresh plant material as a supplement to their normal feed. Observation established that this plant material was consumed in preference to their concurrently supplied normal food. The birds did disperse some of their food and so consumed less than their daily supply of Arabidopsis.

Anti-parasitic effects of transgenic Arabidopsis provided to chicks in their feed These experiments with chicks were carried out with similar experimental conditions to example 5. All were immunosuppressed and infected with *Ascaridia galli* as described earlier. Each bird was weighed immediately before infection and birds of similar weights were paired for the two treatments of untransformed and cystatin-expressing Arabidopsis. Twelve pairs of chicks were established in this way and two birds of one treatment were housed together to avoid incorrect access to the transgenic plants. They were provided from infection ad libitum with water and a proprietry chick starter crumb feed and the plant material supplement on a daily basis. Each pair of birds had access to a mean of 448±25 g of Arabidopsis per week, the majority of which was ingested.

Figure 11:
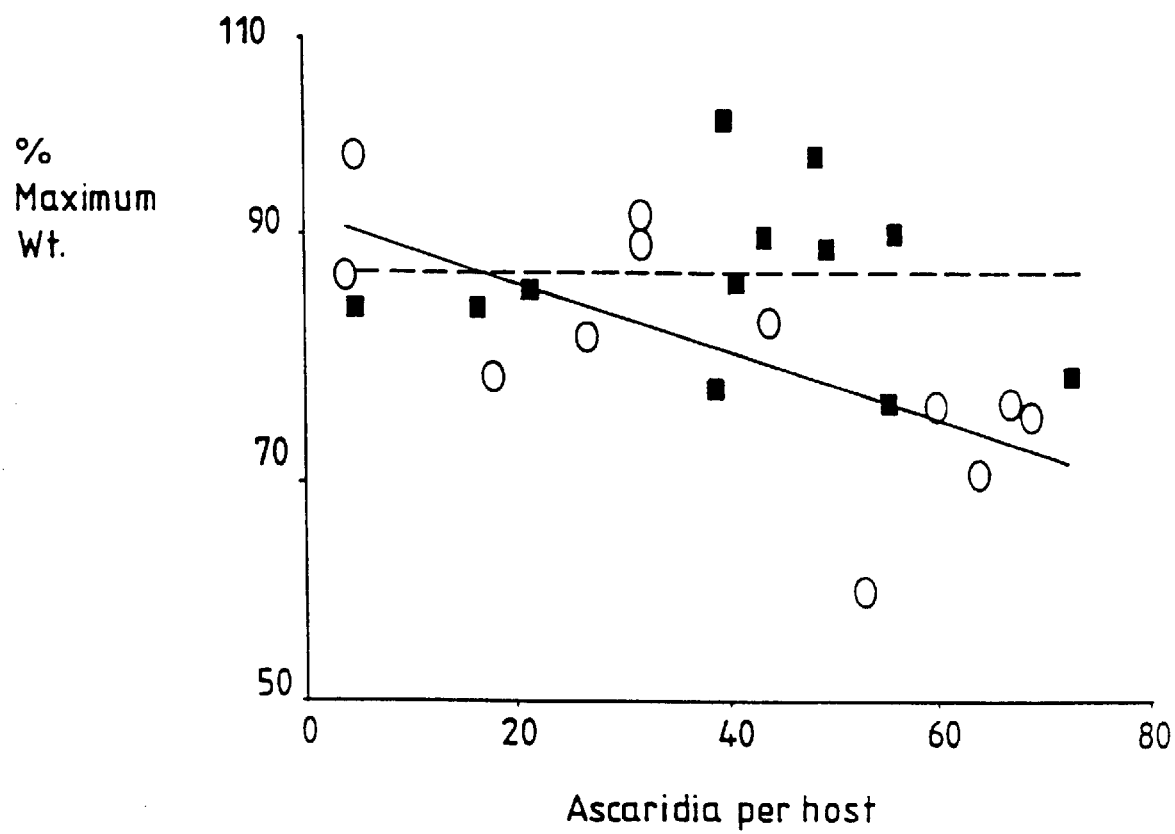
FIG. 11 shows changes in total weight of *A. galli* for chicks fed either on untransformed Arabidopsis or this plant expressing a low level of oryzacystatin I.

After 28 days, the birds were weighed, sacrificed and the *A. galli* were recovered from their intestine as before. These nematodes from each host were fixed in TAF in a series of containers. They were subsequently counted, blotted on filter paper to remove excess fixative and their total wet weight determined using an analytical balance. The weight of each group of nematodes was plotted as a percentage of that for the largest weight in each of the two treatments. This data is plotted against nematodes per host in FIG. 11 which shows changes in weight of *A galli* as a percentage of the maximum value plotted with linear regression lines against the number of nematodes per host for 24 chicks fed either on untransformed Azabidopsis (■) or this plant expressing a low level of oryzacystatin I (o).

There was no significant decrease in weight of *A. galli* with increasing parasitic burden per host for the controls. However this effect did occur for chicks fed on Arabidopsis expressing the oryzacystatin and the downward slope of the regression line was statistically significant (P 0.05).

These results establish that even low levels of a cystatin expressed in only a small part of the food intake of chicks is sufficient for an anti-parasitic effect. The results demonstrate the considerable practical utility of this novel approach to parasite control from several standpoints. The results suggest there may be potential for plant material expressing much higher levels of anti-parasitic protein to be used as an additive to normal food rather as the principal form of dietary intake.

REFERENCES

ABE, K. and ARAI, S. (1985). Purification of a cysteine proteinase inhibitor from rice, *Oryza sativa L. Japonica* Agricultural and Biological Chemistry 49, 3349–3350.

ABE, K., EMORI, Y., KONDO, H., SUZUKI, K. and aRAI, S. (1987a) Molecular cloning of of a cysteine proteinase inhibitor of rice (Oryzacystatin). *J. Biol. Chem.* 262, 16793–16797.

ABE, M. and WHITAKER, J. R. (1988). Purification and characterization of a cysteine proteinase inhibitor from the endosperm of corn. *Agricultural and Biological Chemistry* 52 1583–1584.

ANASTASI, A., BROWN, M. A., KEMEHAVI, A. A., NICKLIN, M. J., SAYERS, C. A., SUNTER, D. C. and BARRETT, A. J. (1983) Cystatin, a protein inhibitor of cysteine proteinases. *Biochemical Journal* 211, 129–138.

ANDRASSY, I. (1956) The determination of volume and weight of nematodes. *Acta Zoologica* (*Hungarian Academy of Science*) 2, 1–15. English translation: Zuckerman, B. M., Brezeski, M. W. and Deubert, K. H. (1967) English Translation of Selected East Europea-n Papers in Nematology. University of Massachusetts, East Wareham, Mass.

BARRETT, A. J. (1980). Introduction: the classification of proteinases. In *Protein Degradation in Health & Disease*. Ciba Foundation Symposium 75 Exerpta Medica.

BARRETT, A. J. and KIRSCHKE, H. (1981) Cathepsin B, Cathepsin H and Cathepsin L. In Lorand, L. (ed) Methods in Enzymology Volume 80, Academic Press, New York.

BAYLIS, H. A., MEGSON, A., MOTTRAM, J. C. and HALL, R. (1992). Characterisation of a gene for a cysteine protease from *Theileria annulata*. *Molecular and Biochemical Parasitology*, 54, 105–108.

BENNETT, K., LEVINE, T., ELLIS, J. S., PEANASKY, R. J., SAMLOFF, I. M., KAY, J. and CHAIN, B. M. (1992) Antigen processing for presentation by class II major histocompatibility complex requires cleavage by cathepsin E. *European Journal of Immunology*, 22, 1519–1524.

BEVAN, M. (1984). Binary Agrobacterium vectors for plant transformation. *Nucleic Acids Research* 12: 8711–8721.

BRADFORD, M. (1976) A rapid and sensitive method for the quantitation of microgram quantities of protein utilising the principle of protein-dye binding. *Analytical Biochemistry* 72, 248–252.

CHAVEZ-OLORTEGUI, C., RESENDE, M. and TAVARES, C. A. P. (1992). Purification and characterization of a 47 kDa protease from *Schistosoma mansoni* cercarial secretion. *Parasitology* 105, 211–218.

CLARKE, M. C., WEI, W. and LINDSEY, K. (1992). High frequency transformation of *Arabidopsis thaliana* by *Agrobacterium tumefaciens*. *Plant Molecular Biology Reporter* 10: 178–189.

COX, G. N., PRATT, D., HAGEMAN, R. and BOISVENUE, R. J. (1990). Molecular cloning and primary sequence of a cysteine protease expressed by *Haemonchus contortus* adult worms. *Molecular and Biochemical Parasitology.* 41, 25–34.

DÜRING, K., HIPPE, S., KREUZALER, F. and SCHELL, J. (1990) Synthesis and self-assembly of a functional monoclonal antibody in transgenic *Nicotiana tabacum*. *Plant Molecular Biology* 15, 284–293.

EAKIN, A. E., MILLS, A. A., HARTH, G., McKERROW, J. H. and CRAIK, C. S. (1992). The sequence, organization, and expression of the major cysteine protease (Cruzain) from *Trypanosoma cruzi*. *The Journal of Biological Chemistry* 11, 7411–7420.

GUILLEY, H. DUDLEY, R. K. JONARD, G., BALAZS, E. and RICHARDS, K. E. (1982) Transcription of Cauliflower Mosaic Virus DNA: Detection of promoter Sequences and Characterization of transcripts. Cell 30: 763.

HAMES, B. D. (1981) An Introduction to polyacrylamide gel electrophoresis. In *Gel Electrophoresis of Proteins; a Practical Approach* (Hames, B. D. and Rickwood, D. eds). Oxford IRL Press; pp1–86.

HEALER, J., ASHALL, F. and MAIZELS, R. M. (1991). Characterization of proteolytic enzymes from larval and adult *Nippostrongylus brasiliensis*. *Parasitology* 103, 305–314.

HEPHER, A. and ATKINSON, M. J. (1992). Nematode Control with Proteinases Inhibitors. European Patent Application Number, 92301890.7; Publication Number 0 502 730A1.

HIATT, A. and MA, J. K-C. (1992) Monoclonal antibody engineering in plants. *FEBS* Letters 307, 71–75.

HIATT, A., CAFFERKEY, R. and BOWDLISH, K. (1989) Production of antibodies in transgenic plants. *Nature* 342, 76–78.

HILDER, V. A., GATEHOUSE, A. M. R., SHEERMAN, S. E., BARKER, R. F. and BOULTER, D. (1987). A novel mechanism of insect resistance engineered into tobacco. *Nature* 330, 160–163.

HILDER, V. A., BARKER, R. F., SAMOUR, R. A., GATEHOUSE, A. M. R., GATEHOUSE, J. A. and BOULTER, D. (1989). Protein and cDNA sequences of Bowman-Birk protease inhibitors from the cowpea (Vigna unguiculata Walp). *Plant Molecular Biology* 13, 701–710.

HORTON, R. M., HUNT, H. D., HO, S. N., PULLEN, J. K. and PEASE, L. R. (1989) Engineering hybrid genes without the use of restriction enzymes—gene splicing by overlap extension. *Gene*, 77, 61–68.

HORTON, R. N. and PEASE, L. R., (1991). Recombination and mutagenesis of DNA sequences using PCR. p. 217–247. In: *"Directed Mutagenesis: A Practical Approach"* M. J. McPherson, ed., IRL Press, Oxford.

KIRSCHKE, H., LANGNER, J., RIEMANN, S., WIEDERANDERS, B., ANSORGE, S. and BOHLEY, P. (1980). Lysosomal cysteine proteinases. In *Protein degradation in health and disease*. Ciba Foundation Symposium 75 Exerpta Medica. LANDSPERGER, W. J., STIREWALT, M. A. and DRESDEN, M. H. (1982). Purification and properties of a proteolytic enzyme from the cercariae of the human trematode parasite *Schistosoma mansoni*. *Biochemical Journal* 201, 137–144.

LUACES, A. L. and BARRETT, A. J. (1988) Affinity purification and biochemical characterization of hitolysin, the major cysteine proteinase of *Entamoeba histolytica*. *Biochemical Journal* 250, 903–909.

MAKI, J. and YANAGISAWA, T. (1986) Demonstration of carboxyl and thiol protease activities in adult *Schistosoma mansoni, Dirofilaria immitis, Angiostrongylus cantonensis* and *Ascaris suum*. *Journal of Helminthology* 60, 31–37.

MANIATIS, T., FRISCH, E. F. and SANBROOK, J. (1982). *Molecular Cloning: a laboratory manual*. New York: Cold Spring Harbor Laboratory Press.

MARTZEN, M. R., MCMULLEN, B. A., SMITH, N. E., FUJIKAWA, K. and PEANASKY, R. J. (1990). Primary structure of the major pepsin inhibitor from the intestinal parasitic nematode *Ascaris suum*. *Biochemistry* 29, 7366–7372.

MASON, H. S., LAM, D. M-K. and ARNTZEN, C. J. (1992) Expression of hepatitis B surface antigen in transgenic plants. *Proceedings of the National Academy of Sciences of the United States, of America* 89, 11745–11749.

MASOUD, S. A., JOHNSTONE, L. B., WHITE, F. F. and REECK, G. R. (1993) Expression of a cysteine proteinase inhibitor (oryzacystatin-I) in transgenic tobacco plants. *Plant Molecular Biology* 21, 665–663.

MBAWA, Z. R., GUMM, I. D., SHAW, E. and LONSDALE-ECCLES, J. D. (1992) Characterisation of a cysteine protease from bloodstream forms of *Trypanosoma congolense*. *European Journal of Biochemistry* 204, 371–379.

McKEE, H. S. (1962) "Nitrogen Metabolism in Plants", Clarendon Press, Oxford.

McKERROW, J. H. (1989). Parasite proteases. *Experimental Parasitology* 68, 111–115.

MOFFAT, A. S. (1993) Genetically engineered plants point toward edible vaccines. Genetic Engineering News, June 15, pp 1 and 19.

ODELL, J. T., NAGY, F, CHUA, N-H. (1985) Identification of DNA sequences required for activity of the cauliflower mosiac virus 35S promoter. *Nature* 313: 810.

PAWLOWSKI, Z. S. (1990) Asacariasis In: "Tropical and Geographical Medicine", Warren, K. S. and Mahmoud, A. A. F., eds. 2nd Edn. McGraw-Hill, New York.

PRATT, D., COX, G. N., MILHAUSEN, M. J. and BOISVENUE, R. J. (1990) A developmentally regulated cysteine protease gene family in *Haemonchus contortus*. *Molecular and Biochemical Parasitology*, 43 , 181–191.

RAY, C., and McKERROW, J. H. (1992). Gut-specific and developmental expression of a *Caenorhabditis elegans* cysteine protease gene. *Molecular and Biochemical Parasitology*, 51, 239–249.

RICHER, J. K., SAKANARI, J. A., FRANK, G. R., and GRIEVE, R. B. (1992). *Dirofilaria immitis*: proteases produced by third-stage and fourth-stage larvae. *Experimental Parasitology* 75, 213–222.

ROSENTHAL, P. J., and NELSON, R. G. (1992). Isolation and characterization of a cysteine proteinase gene of *Plasmodium falciparuzm*. *Molecular and Biochemical Parasitology* 51, 143–152.

SAKANARI, J. A. (1990). Anisakis—from the platter to the microfuge. *Parasitology Today* 6, 323–327.

SAKANARI, J. A., STAUNTON, C. E., EAKIN, A. E., CRAIK, C. S. and McKERROW, J. H. (1989). Serine proteases from nematode and protozoan parasites.: isolation of sequence homologs using generic molecular probes. *Proceedings of the National Academy of Sciences, USA* 86, 4863–4867.

SAMBROOK, J., FRITSCH, E. F. and MANIATIS, T. (1989) Molecular Cloning, a Laboratory Manual, Second Edition. Cold Spring Harbor Laboratory Press, Cold Spring Harbor, New York.

SARKIS, G. J., KURPIEWSKI, M. R., ASHCOM, J. D., JEN-JACOBSON, L. and JACOBSON, L. A. (1988) Proteases of the nematode *Caenorhabditis elegans*. *Archives of Biochemistry and Biophysics* 261, 80–90.

SNEDECOR, G. W. and COCHRAN, W. G. (1989) Statistical Methods, Eighth Edition. Iowa State University Press, Ames, Iowa.

VALVEKENS, D., VAN MONTAGU, M. and Van LIJSEBETTENS, M. (1988). *Agrobacterium tumefaciens*-mediated transformation of *Arabidopsis thaliana* root explants by using kanamycin selection. *Proc. Natl. Acad. Sci. USA* 85: 5536–5540.

WEN-JUN, S. and FORDE B. G. (1989). Efficient transformation of Agrobacterium spp. by high voltage electroporation. *Nucleic Acids Research* 17: 83–85.

WOOD, B. (ed) (1988). The nematode *C. elegans*. New York: Cold Spring Harbor Laboratory Press. pp 606.

We claim:

1. A method for combating an infection by an animal parasite in a host animal which comprises delivering an anti-parasitic protein to the parasite or a locus thereof by administering the protein to the host animal as a medicament or as a food wherein the antiparasitic protein exhibits an anti-parasitic action which does not involve the immune system of the host and wherein said anti-parasitic protein is an enzyme of said parasite.

2. A method according to claim 1 wherein said animal parasite is selected from the group consisting of helminths and protozoans.

3. A method according to claim 2 wherein said animal parasite is a nematode.

4. A method according to claim 1 wherein said anti-parasitic protein is an inhibitor of a digestive enzyme of said parasite.

5. A method according to claim 4 wherein said anti-parasitic protein is a cysteine protease inhibitor.

6. A method according to claim 4 wherein said anti-parasitic protein is a cysteine protease inhibitor from maize or rice.

7. A method according to claim 1 wherein said anti-parasitic protein is expressed by a transgenic plant.

8. A method according to claim 7 wherein said transgenic plant is a dietary crop for said host animal.

9. A composition adapted for oral, parenteral or topical administration to a host animal, which composition combats a parasitic infection by an animal parasite to which said host animal is subject, which composition comprises an anti-parasitic protein directed against said animal parasite, said anti-parasitic protein having been expressed by a transgenic plant, wherein said anti-parasitic protein is a cysteine protease inhibitor from maize or rice.

10. A composition according to claim 9 wherein said transgenic plant is a dietary crop for said host animal.

11. A composition according to claim 10 wherein said anti-parasitic protein is incorporated into the composition in the form of parts of the transgenic plant.

12. A composition according to claim 10 wherein said animal parasite is selected from the group consisting of helminths and protozoans.

13. A composition according to claim 12 wherein said animal parasite is a nematode.

14. A composition according to claim 9 wherein said anti-parasitic protein is extracted from the transgenic plant prior to incorporation into the composition.

15. A composition according to claim 9 in a form adapted for oral administration.

16. A composition according to claim 15 in the form of a food or a medicament for said host animal.

17. A process for the manufacture of a composition adapted for administration to a host animal as a medicament or a food and which combats an infection by an animal parasite to which said host animal is subject, which process comprises processing a transgenic plant into a medicament or a food for said host animal, said transgenic plant being transformed with DNA encoding an anti-parasitic protein against said animal parasite and expressing said protein within the transgenic plant, wherein said anti-parasitic protein is an inhibitor of an enzyme of said parasite.

18. A process according to claim 17 wherein said animal parasite is selected from the group consisting of helminths and protozoans.

19. A process according to claim 17 wherein said animal parasite is a nematode.

20. A process according to claim 18 wherein said anti-parasitic protein is an inhibitor of a digestive enzyme of said parasite.

21. A process according to claim 20 wherein said anti-parasitic protein is a cysteine protease inhibitor.

22. A process according to claim 21 wherein said anti-parasitic protein is a cysteine protease inhibitor from maize or rice.

23. A process according to claim 17 wherein said transgenic plant is a dietary crop for said host animal.

24. A transgenic plant transformed with a DNA encoding for a cysteine protease inhibitor from maize or rice wherein the plant, when ingested by a host animal infected by a parasite producing a protease, delivers to the parasite a cysteine protease inhibitor in an amount and form which is effective to inhibit the activity of the parasite originated protease and wherein the plant is a dietary crop for the host animal.

25. A method for combating an infection by an animal parasite in a host animal which comprises delivering an anti-parasitic protein to the parasite or a locus thereof by administering the protein to the host animal as a medicament or as a food wherein the animal parasite is a helminth or a protozoan, and wherein the antiparasitic protein exhibits an anti-parasitic action which does not involve the immune system of the host and wherein said anti-parasitic protein is an enzyme of said parasite.

26. A method for combating an infection by an animal parasite in a host animal which comprises delivering an anti-parasitic protein to the parasite or a locus thereof by administering the protein to the host animal as a medicament or as a food wherein the animal parasite is a nematode, and wherein the antiparasitic protein exhibits an anti-parasitic action which does not involve the immune system of the host and wherein said anti-parasitic protein is an enzyme of said parasite.

* * * * *